(12) United States Patent
Sharon et al.

(10) Patent No.: US 6,743,194 B2
(45) Date of Patent: Jun. 1, 2004

(54) MULTI-COMPARTMENT SYRINGE

(76) Inventors: Igal Sharon, 5 Adar Street, Caesaria (IL); Yohanan Maggeni, Ilaoya, Lower Galilee (IL)

( * ) Notice: Subject to any disclaimer, the term of this patent is extended or adjusted under 35 U.S.C. 154(b) by 0 days.

(21) Appl. No.: 10/108,952

(22) Filed: Mar. 28, 2002

(65) Prior Publication Data

US 2003/0187388 A1 Oct. 2, 2003

(51) Int. Cl.[7] .................. A61M 37/00; A61M 5/00; A61M 5/315
(52) U.S. Cl. .................. 604/89; 604/191; 604/218
(58) Field of Search .................. 604/38, 82, 89–91, 604/191, 218, 221, 222

(56) References Cited

U.S. PATENT DOCUMENTS

| | | | | |
|---|---|---|---|---|
| 2,761,447 A | * | 9/1956 | Hersee | 604/89 |
| 3,016,896 A | | 1/1962 | Van Sickle | 128/218 |
| 3,511,239 A | | 5/1970 | Tuschhoff | 128/218 |
| 3,662,753 A | * | 5/1972 | Tassell | 604/89 |
| 3,749,084 A | | 7/1973 | Cucchiara | 128/2 F |
| 3,766,917 A | | 10/1973 | Wimmer | 128/218 M |
| 3,881,484 A | | 5/1975 | Gidcumb, Jr. | 128/218 M |
| 3,985,122 A | | 10/1976 | Topham | 128/2 F |
| 4,030,498 A | * | 6/1977 | Tompkins | 604/152 |
| 4,185,628 A | * | 1/1980 | Kopfer | 604/82 |
| 5,716,339 A | | 2/1998 | Tanaka et al. | 604/89 |
| 5,899,881 A | | 5/1999 | Grimard et al. | 604/89 |

FOREIGN PATENT DOCUMENTS

GB   WO0053244   9/2000   .......... A61M/5/315

* cited by examiner

Primary Examiner—Brian L. Casler
Assistant Examiner—Catherine Serke
(74) Attorney, Agent, or Firm—Pennie & Edmonds LLP

(57) ABSTRACT

A multi-compartment syringe for storing two or more substances in separate compartments comprises a tubular body having an opening at each end and a plunger. The body has two or more compartments defined along its length, where each compartment has a successively larger diameter. The plunger has a plunger head at one end that partitions the first and second compartments and one or more bungs, slidable along the plunger's shaft, for partitioning each of the other compartments. The plunger head and the bungs can be unsealed to establish a flow communication between the compartments.

29 Claims, 26 Drawing Sheets

MULTI-COMPARTMENT SYRINGE

FIELD OF THE INVENTION

The present invention relates to a multi-compartment syringe and more particularly to a pre-filled single barreled multi-compartment syringe that stores at least two substances in separate compartments until ready to be mixed just prior to use.

SUMMARY OF THE INVENTION

The multi-compartment syringe according to the present invention is a single barreled syringe that may be configured to store two or more components of a medicament or other formulation separately in hermetically sealed compartments until just prior to use.

When ready to mix the contents of the pre-filled syringe, the seal(s) partitioning the compartments can be easily unsealed, establishing flow communication between the compartments so that the contents of each compartment can be mixed to form the medicament.

A two-compartment syringe device according to one embodiment of the present invention includes a syringe body having an opening at each of its top and bottom ends and a shoulder located between the top and the bottom ends. The shoulder delineates the syringe body into a top compartment and a bottom compartment.

A base ridge located between the shoulder and the bottom end of the syringe body further defines the syringe body into a bottom-compartment sidewall portion and a base-skirt portion. The bottom-compartment sidewall portion is between the shoulder and the base ridge and the base-skirt portion is between the base ridge and the bottom end of the syringe body. The bottom-compartment sidewall portion has a larger diameter than the top-compartment sidewall portion and the base-skirt portion has a larger diameter than the bottom-compartment sidewall portion.

A plunger having a shaft, a distal end, a proximal end, and a plunger at the distal end is provided within the syringe body. The plunger head is configured and adapted to form a slidable hermetic seal when it engages the top-compartment sidewall. The plunger is axially translatable between a first position where the plunger head is slidably sealingly engaged within the top-compartment sidewall, dividing the syringe body into a top compartment and a bottom compartment, and a second position where the plunger head is disengaged from the top-compartment sidewall portion establishing a flow communication between the top and bottom compartments.

A bung having an aperture is also provided. The plunger shaft is slidably disposed within the aperture of the bung so that the bung is slidable along the plunger shaft between a sealed position, hermetically sealing the bottom-end opening, and an unsealed position where the bottom-end opening is not sealed. When the bung is in its sealed position, it is substantially positioned within the base-skirt portion of the syringe body and the plunger can be axially translated between its first position and the second position without dislodging the bung from the base-skirt portion. To enable the translation of the plunger without dislodging the bung, the bung may be configured and adapted so that the friction between the bung and the syringe body is greater than the friction between the bung and the plunger shaft.

The syringe is assembled and filled, according to one method, by first orienting the body with the two-compartment embodiment of the syringe in an upright position with its top-end opening pointing upwardly. The plunger is then inserted into the syringe body, plunger-head portion first, until the plunger head engages the top-compartment sidewall. This forms a hermetic seal at the bottom of the top compartment near the shoulder portion. The top compartment is then filled with a first component of a medicament, preferably a liquid, through the top-end opening and sealed with a suitable top sealing member or assembly. To prevent any degradation of the first component from prolonged exposure to air during storage, the top compartment may be sized to fill completely with the first component liquid, minimizing or eliminating any air pockets inside the top compartment. Alternatively, any unfilled space in the top compartment may be filled with a material, such as nitrogen gas for example, which is inert with the first component.

Where the first component of a medicament is a liquid, the top compartment may be filled by inserting the plunger completely to the end of the top compartment, immersing the open top end in the liquid, then drawing the liquid into the top compartment by pulling the plunger back to its sealed position between the compartments.

Next, the syringe device may be turned 180 degrees, with the sealed top end oriented downwardly, so that the bottom-end opening is facing up. The bottom compartment is filled with a second component of the medicament through the bottom-end opening and sealed with the bung. The second component may be a liquid or a powdered solid substance. In this embodiment where a bung seals the bottom opening, the second component may be placed in the bottom compartment in a hydrated form and dried using a lyophilization process. Before the lyophilization process begins, the bung is brought close to the base-skirt portion so that it almost fits into the base-skirt portion and the substantial portion of the bung remains outside the base-skirt portion. The vacuum created in the bottom compartment during the lyophilization process pulls the bung completely into the base-skirt portion sealing the bottom-end opening.

Alternatively, the bottom opening of the syringe body may be configured and adapted to be sealed using a bottom closure member that can be screwed onto the syringe body's bottom-end opening.

A syringe device having three compartments may also be provided for separately storing three components of a medicament for storage until ready for use. In this embodiment the syringe device has an additional compartment situated between the top and bottom compartments. As with the two-compartment embodiment, each compartment section has progressively larger diameter where the top compartment closest to the top-end opening has the smallest diameter and the bottom compartment has the largest diameter. The hermetic seal between the top and the middle compartment is formed by the plunger head and the top-compartment sidewall. The hermetic seal between the middle compartment and the bottom compartment is formed by an additional bung that sealingly engages the portion of the syringe body between the middle compartment and the bottom compartment where the diameter of the syringe body changes. The present invention also includes the method of assembling and filling such a syringe device.

The invention will now be described in more detail with references to two and three-compartment embodiments of the syringe device of the invention. It would be appreciated by those skilled in the art that the same principle is also applicable to syringe devices having more than three compartments.

BRIEF DESCRIPTION OF THE DRAWINGS

The features and advantages of the present invention will become more readily apparent from the following detailed description of the invention in which like elements are labeled similarly and in which.

DETAILED DESCRIPTION OF THE INVENTION

Figure 1:
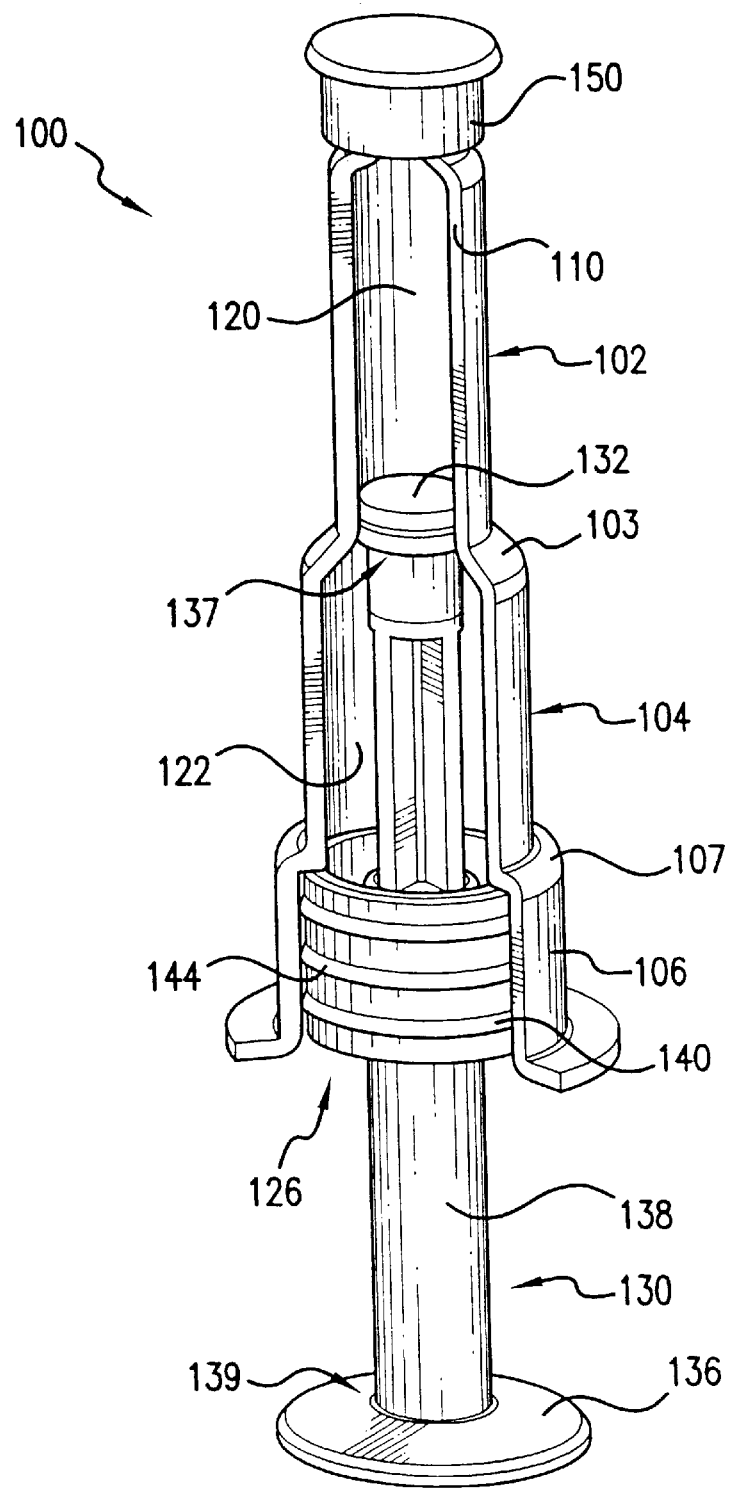
FIG. 1 is a perspective view of an embodiment of the syringe device of the invention having two compartments where the syringe body is illustrated as being translucent in order to show the internal structures of the syringe.

FIGS. 1–7 disclose a syringe device 100 according to one embodiment having two-compartments. FIG. 1 illustrates the syringe device comprising a syringe body 110 having two open ends: a top-end opening 124 (see FIG. 3) and a bottom-end opening 126. The syringe body 110 has three main sections, a top-compartment sidewall 102, a bottom-compartment sidewall 104, and a base-skirt portion 106, with the diameter of the syringe body increasing progressively with each section. In other words, the diameter of the base-skirt portion 106 is larger than the diameter of the bottom-compartment sidewall 104, which in turn, is larger than the diameter of the top-compartment sidewall 102.

Between the top-compartment sidewall 102 and the bottom-compartment sidewall 104 is a shoulder 103 where the diameter of the syringe body 110 changes from the top-compartment sidewall 102 to the bottom-compartment sidewall 104. Between the bottom-compartment sidewall 104 and the base-skirt portion 106 is a base ridge 107 where the diameter of the syringe body 110 increases from the diameter of the bottom-compartment sidewall 104 to the larger diameter of the base-skirt portion 106.

The syringe device 100 also includes a plunger 130. The plunger 130 consists of a plunger shaft 138, a distal end 137, and a proximal end 139 and is provided with a plunger head 132 at distal end 137. The plunger head 132 sealingly engages the inside wall surface of the top-compartment sidewall 102 to form a hermetic seal that forms a partition between the top compartment 120 and the bottom compartment 122. The plunger head 132 is preferably made of an elastomer having characteristics (e.g. hardness, elasticity, etc.) that is suitable to provide the desired sealing quality. The particular elastomer selected for the plunger head 132 should also be chemically inert with respect to the particular medicament or components with which the plunger head 132 may come in contact. A thumb rest 136 may be provided on proximal end 139 of the plunger 130 with which a user may urge the plunger 130 into the syringe body 110 to dispense the contents of the syringe device 100.

Figure 2:
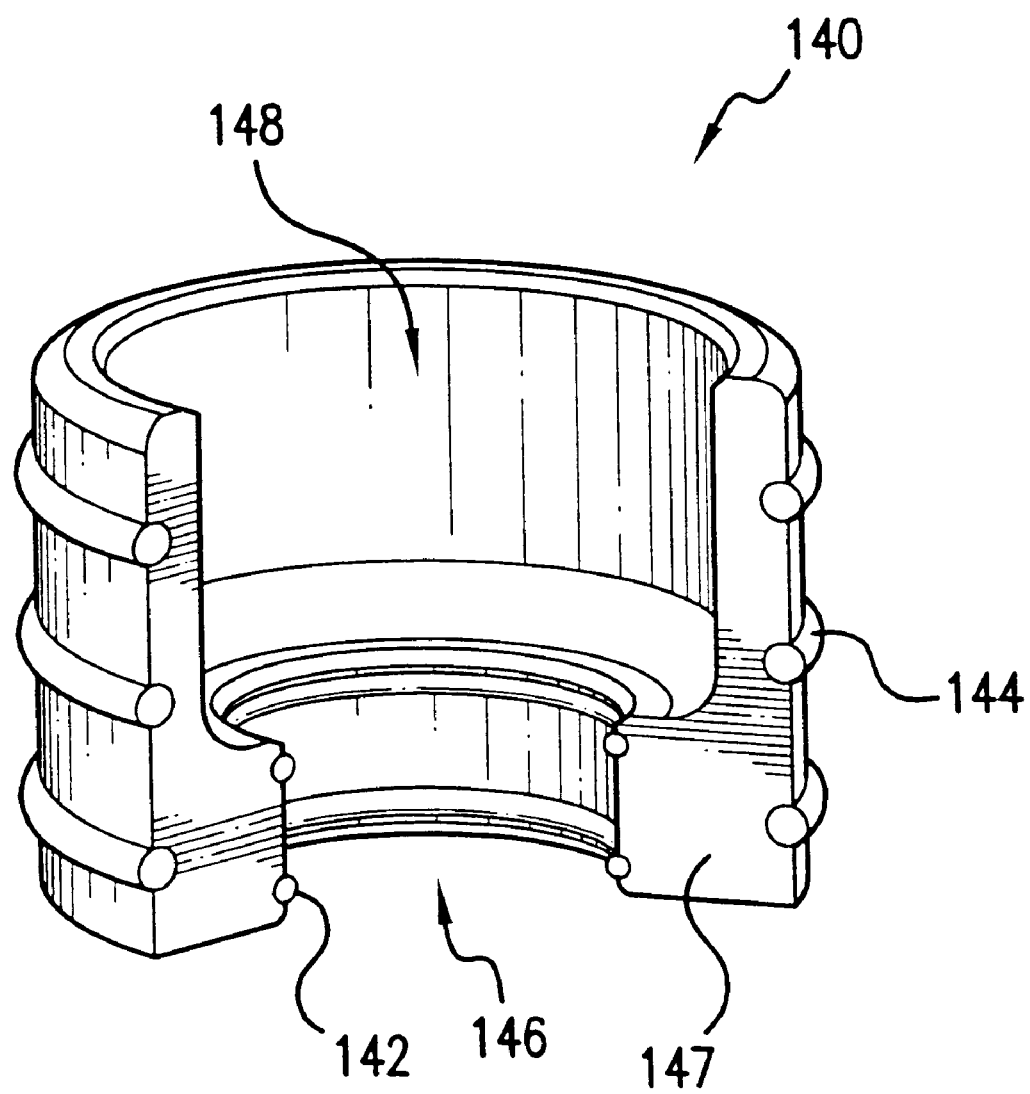
FIG. 2 is a sectional view of the bung from the syringe device of FIG. 1.

The syringe device 100 also includes a bung 140 for sealing the bottom-end opening 126. FIG. 2 illustrates a detailed cross-section of the bung 140. The bung 140 has a central aperture 146 through its axial center so that the plunger 130 is received through the central aperture and the bung 140 can be moved up and down the plunger shaft 138. The outer surface of the bung 140 is provided with a plurality of outer sealing ribs 144 for sealingly engaging the inside surface of the base-skirt portion 106 and sealing the bottom-end opening 126. The side wall of the central aperture 146 is provided with a plurality of inner sealing ribs 142 for sealingly engaging the plunger shaft 138. These sealing ribs may be configured to form hermetic seals with the mating surface through compression. When assembled, the bung 140 is positioned on the plunger shaft 138 between the thumb rest 136 and stopper tab 134.

When the bung 140 is positioned in its sealed position, preferably the plunger 130 can be withdrawn partially from the syringe body 110 without dislodging the bung 140 from its sealed position within the base-skirt portion 106. This allows the plunger head 132 to be disengaged from the top-compartment sidewall 102 to establish communication between the top and the bottom compartments without unsealing the bottom-end opening.

To enable the translation of the plunger 130 without dislodging the bung 140 from the bung's sealed position within the base-skirt portion 106, the bung 140 may be configured and adapted so that the friction between the bung 140 and the base-skirt portion 106 is greater than the friction between the bung 140 and the plunger shaft 138.

The bung 140 is provided with a well 148 so that the inner sealing ribs 142 are confined to the limited surface of lower portion 147 of the bung 140. In this embodiment, a greater number of outer sealing ribs 144 are provided compared to the inner sealing ribs 142. Where the dimensions of the outer and inner sealing ribs are such that the static friction between each sealing rib and its mating surface, the base-skirt portion or the plunger shaft, are substantially equal, this configuration provides greater friction between the bung 140 and the base-skirt portion 106 than the friction between the bung 140 and the plunger shaft 138.

Although in the particular example of the bung 140 illustrated in FIG. 2, the frictional forces between the bung and the syringe body 110 and the plunger shaft 138 may be controlled by varying the number of the sealing ribs at each sealing surfaces, it will be obvious to one of ordinary skill in the art that the same result could be achieved by many other methods. For example, the dimensions of the sealing ribs, such as their widths and thicknesses, may be varied to achieve the desired frictional forces at each sealing interface without necessarily varying the number of the sealing ribs.

FIG. 1 illustrates a fully assembled syringe device 100 in a storage configuration. The plunger 130 is positioned inside the syringe body 110 so that the plunger head 132 sealingly engages the top-compartment sidewall 102, in proximity to the shoulder 103. Thus, the plunger head 132 partitions the syringe body 110 into a top compartment 120 and a bottom compartment 122. The seal formed by the plunger head 132 and the top-compartment sidewall 102 may be hermetic so that two components of a medicament or other formulation may be stored separate in each compartment until ready to be mixed.

In this fully assembled and ready-for-storage configuration, the bung 140 resides substantially within the base-skirt portion 106 so that the plurality of outer sealing ribs 144 sealingly engage the inside wall of the base-skirt portion 106 hermetically sealing the bottom-end opening 126. The base ridge 107 functions as a stopper preventing the bung 140 from traveling too far into the syringe body 110.

Figure 3:
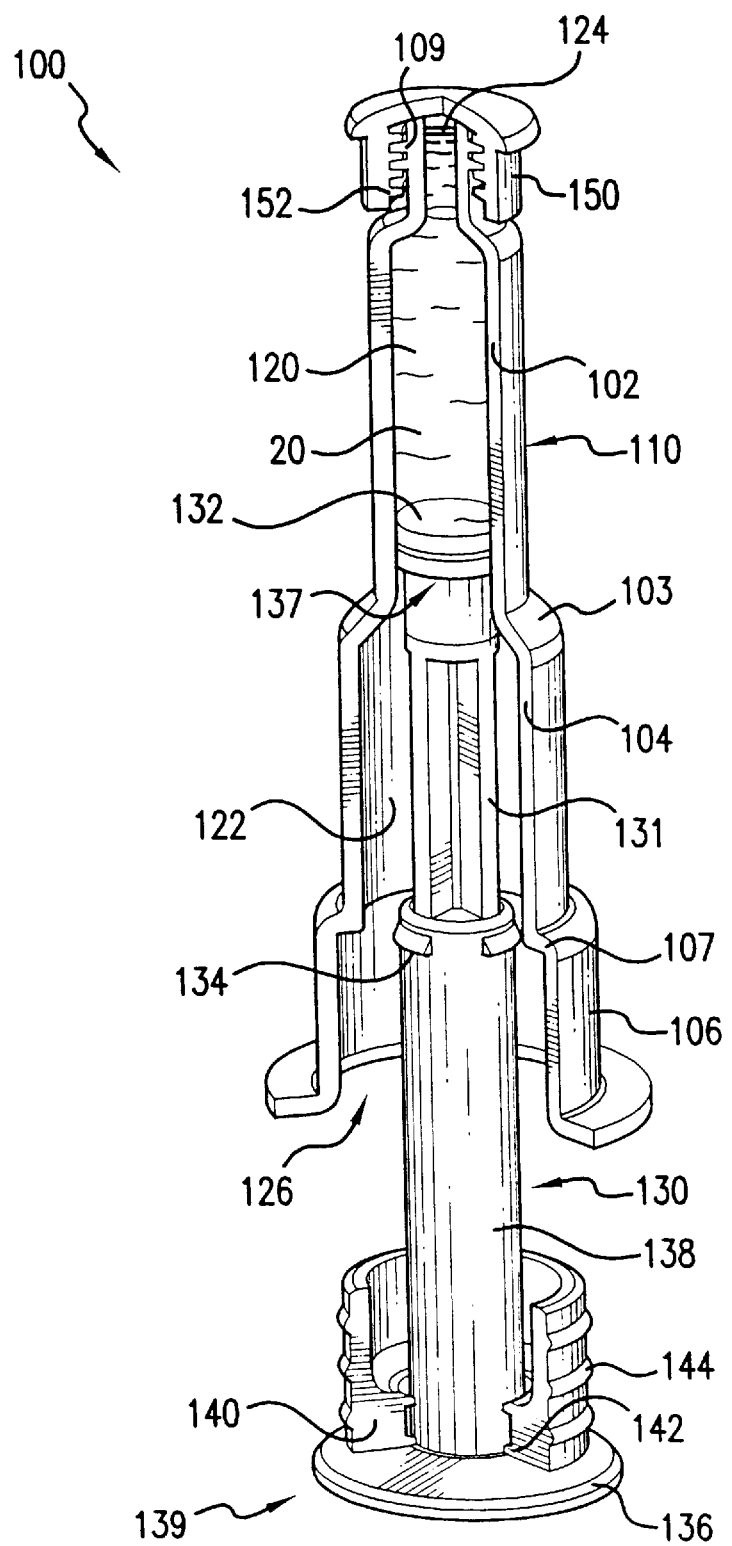
FIG. 3 is a sectional view of the syringe device of FIG. 1, illustrating the syringe device in an interim stage in the process of filling and assembling the syringe device where its top compartment has been filled with a desired substance and sealed.

The top-end opening 124 is removably sealed with a top sealing member or assembly which is configured to be removable when desired; for example, when the contents of the syringe device 100 have been mixed and are ready to be dispensed. The top sealing member 150 may be a cap as shown in FIG. 3. In this embodiment, the top sealing member 150 is a screw cap. The cap 150 is provided with screw threads 152 and the top-end opening 124 of the syringe body 110 is also provided with screw threads 109 so that the cap 150 can be screwed onto the syringe body 110 to seal the top end opening 124.

It will be apparent to those skilled in the art that a top sealing member 150 and the top-end opening 124 may be configured to sealingly engage each other in a variety of ways that may be appropriate and suitable for a particular application. For example, the top sealing member 150 may be a foil or a membrane made of a suitable material that may be heat sealed along the rim 125 of the top-end opening 124. The heat sealed membrane may be peeled away to unseal the top-end opening 124 when the syringe device 100 is ready to be used.

The process of assembling and filling the syringe device 100 will now be described with the aid of FIGS. 3 and 4. A syringe body 110 is oriented in an upright position with its top-end opening 124 pointing upwardly. A plunger 130 is then inserted through bottom opening 126 into the syringe body 110 plunger head 132 first, until the plunger head 132 engages the top-compartment sidewall 102. The engagement of the plunger head 132 with the top-compartment sidewall 102 forms a hermetic seal at the bottom of the top compartment 120 in proximity to the shoulder 103.

The top compartment 120 is then filled with a first component of a medicament through the top-end opening 124 and sealed with the cap 150. In this embodiment of the invention, the first component is preferably the liquid component of the medicament. To prevent any degradation of the first component from prolonged exposure to air during storage, the top compartment 120 may be filled completely with the first component liquid, minimizing or eliminating any air pockets inside the top compartment 120 when sealed with the cap 150. In the alternative, the filling process may be conducted under a vacuum or an inert gas environment so that even if the top compartment is not completely filled with the first component liquid, there would not be any air trapped inside the top compartment after being sealed with the cap 150.

The top compartment may also be filled by inserting the plunger completely to the end of the top compartment, immersing the open top end in the first component liquid, then drawing the liquid into the top compartment by pulling the plunger back to the sealed position between the compartments. The syringe body 110 may be dimensioned so that when the plunger is withdrawn back to its sealed position, the top compartment 120 will be filled with a predetermined desired amount of the first component 20.

The cap 150 is preferably configured and adapted to form a hermetic seal along the rim 125 of the top-end opening 124. But, it would be apparent to one of ordinary skill in the art that the particular requirement for the quality of the seal formed by the cap 150 would be dictated by the particular application for which the syringe device is intended. This would be true for the seal formed by the bung 140 at the bottom-end opening 126 also and for the seal formed by the plunger head 132 between the top compartment 120 and the bottom compartment 122.

FIG. 3 is a sectional illustration of the syringe device 100 at this stage of the assembly. The top compartment 120 has been filled with the first component of a medicament and the top-end opening has been sealed with the cap 150 and at the opposite end by the plunger head 132.

At this stage of the assembly, the syringe device 100 may be turned 180 degrees, with the capped end oriented down, so that the bottom compartment 122 may be filled. At this stage of the assembly, the bung 140 is not yet in its sealed position and it is positioned near the thumb rest 136 of the plunger 130 so that the bottom-end opening 126 is free of any encumbrances. The static frictional force between the plunger shaft 138 and inner sealing ribs 142 on the bung 140 will keep the bung 140 from sliding down the plunger shaft 138.

The bottom compartment 122 is then filled with a second component of the medicament through the bottom-end opening 126. The bottom compartment 122 may then be sealed by sliding the bung 140 along the plunger shaft 138 and into the base-skirt portion 106. However, this sealing operation is preferably carried out in a vacuum so that air pressure inside the bottom compartment does not prevent the bung 140 from sliding into the base-skirt portion 106. The second component may be a liquid or a powder substance.

Alternatively, the bottom compartment 122 may be filled using a lyophilization process (also known as freeze drying). After the second component of the medicament in a hydrated form is placed inside the bottom compartment 122, the bung 140 is positioned on the plunger shaft 138 so that it is almost fitted into the base-skirt portion 106 so that substantial portion of the bung 140 is still outside the base-skirt portion 106. And during the lyophilization process, the vacuum created in the bottom compartment 122 pulls the bung 140 completely into the base-skirt portion 106 forming a hermetic seal at the bottom-end opening 126.

Figure 4:
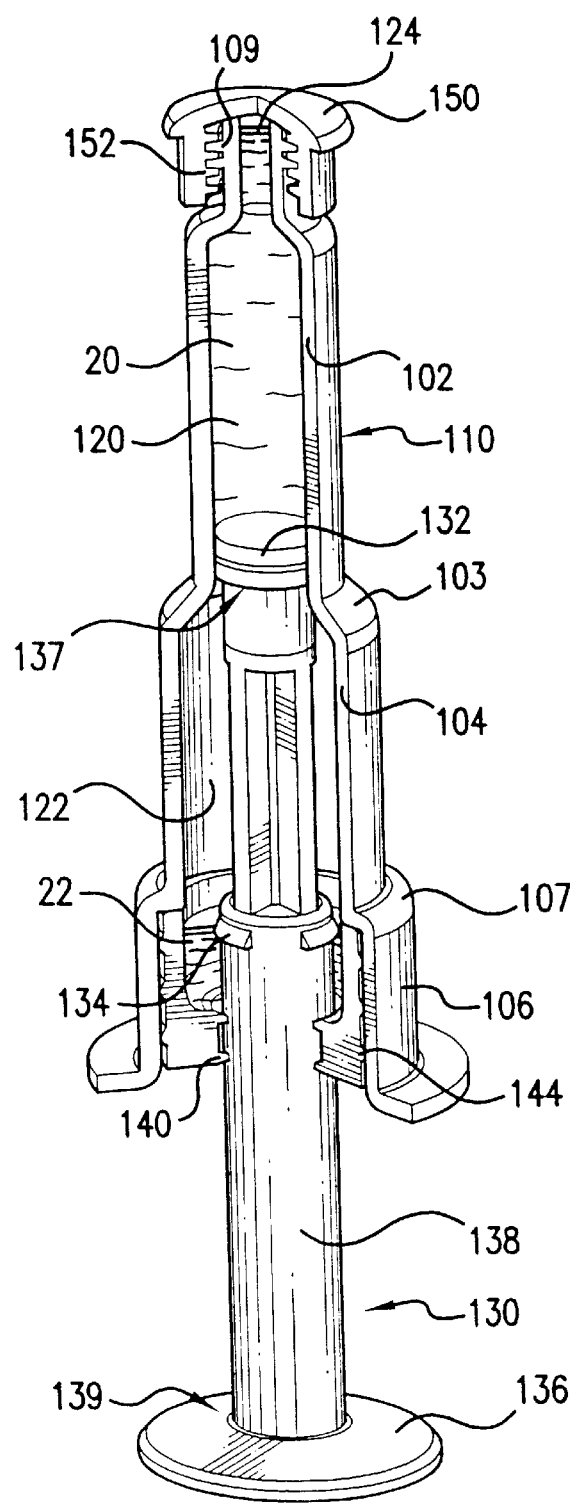
FIG. 4 is a sectional view of the syringe device of FIG. 3, illustrating the syringe device in a next interim stage in the process of filling and assembling the syringe device where its bottom compartment has been filled and sealed, ready for use.

FIG. 4 illustrates the fully assembled syringe device 100 in the storage configuration. The syringe device 100 now consists of two completely sealed compartments—the top compartment 120 and the bottom compartment 122—where each compartment is holding a component of a medicament for storage until ready to be mixed just prior to use.

The quality of the seal formed between the bung's inner sealing ribs 142 and the plunger shaft 138 and the quality of the seal formed between the bung's outer sealing ribs 144 and the base-skirt portion 106 should be configured so that the two seals combined can provide the quality of the sealing desired for the bottom compartment 122. The quality of the seals may be controlled by the appropriate selection of the elastomer materials for the bung 140 and other parameters such as the surface finish of the plunger shaft 138 and the inside surface of the base-skirt portion 106. The material selection criteria are also equally applicable to the plunger head 132.

Figure 5:
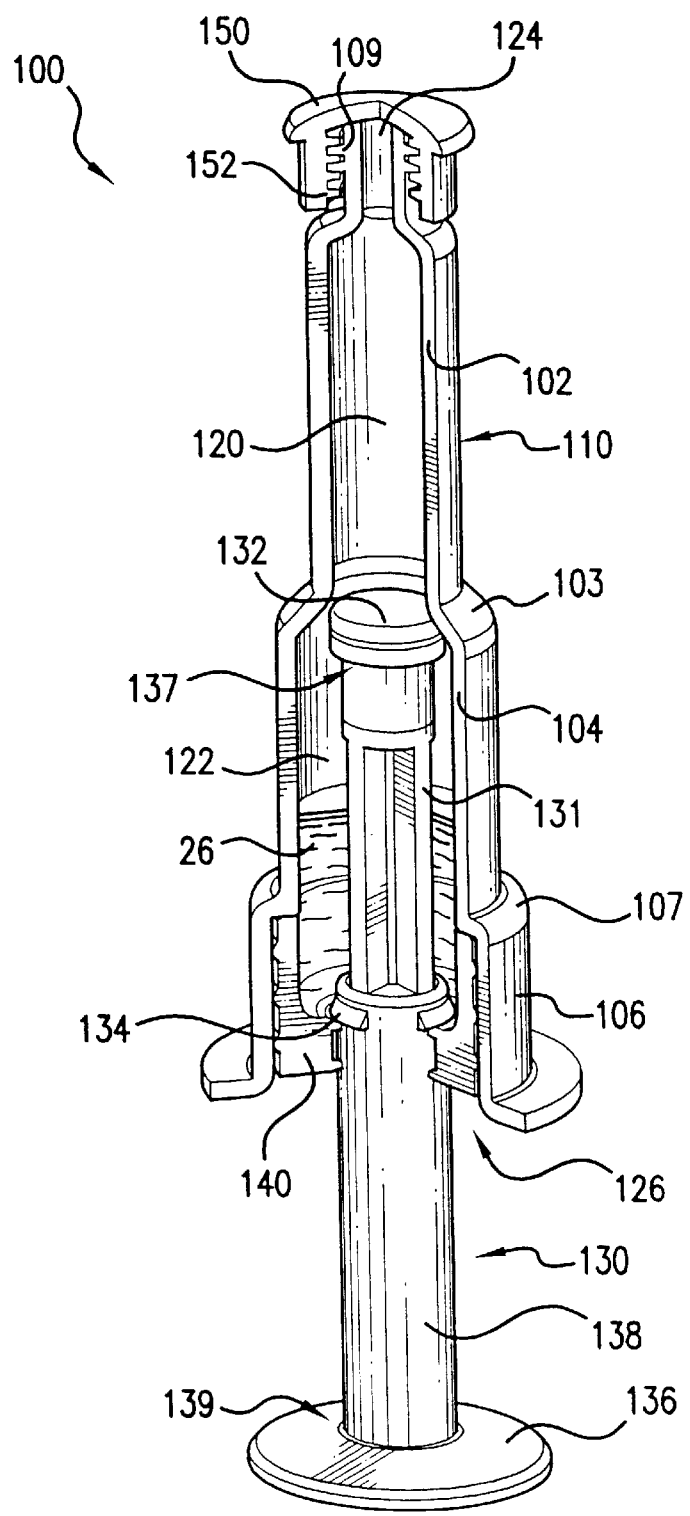
FIG. 5 is a sectional view of the syringe device of FIG. 4, illustrating the plunger retracted into the bottom compartment so that the two compartments are in communication with one another allowing the contents of the two compartments to mix.
Figure 6:
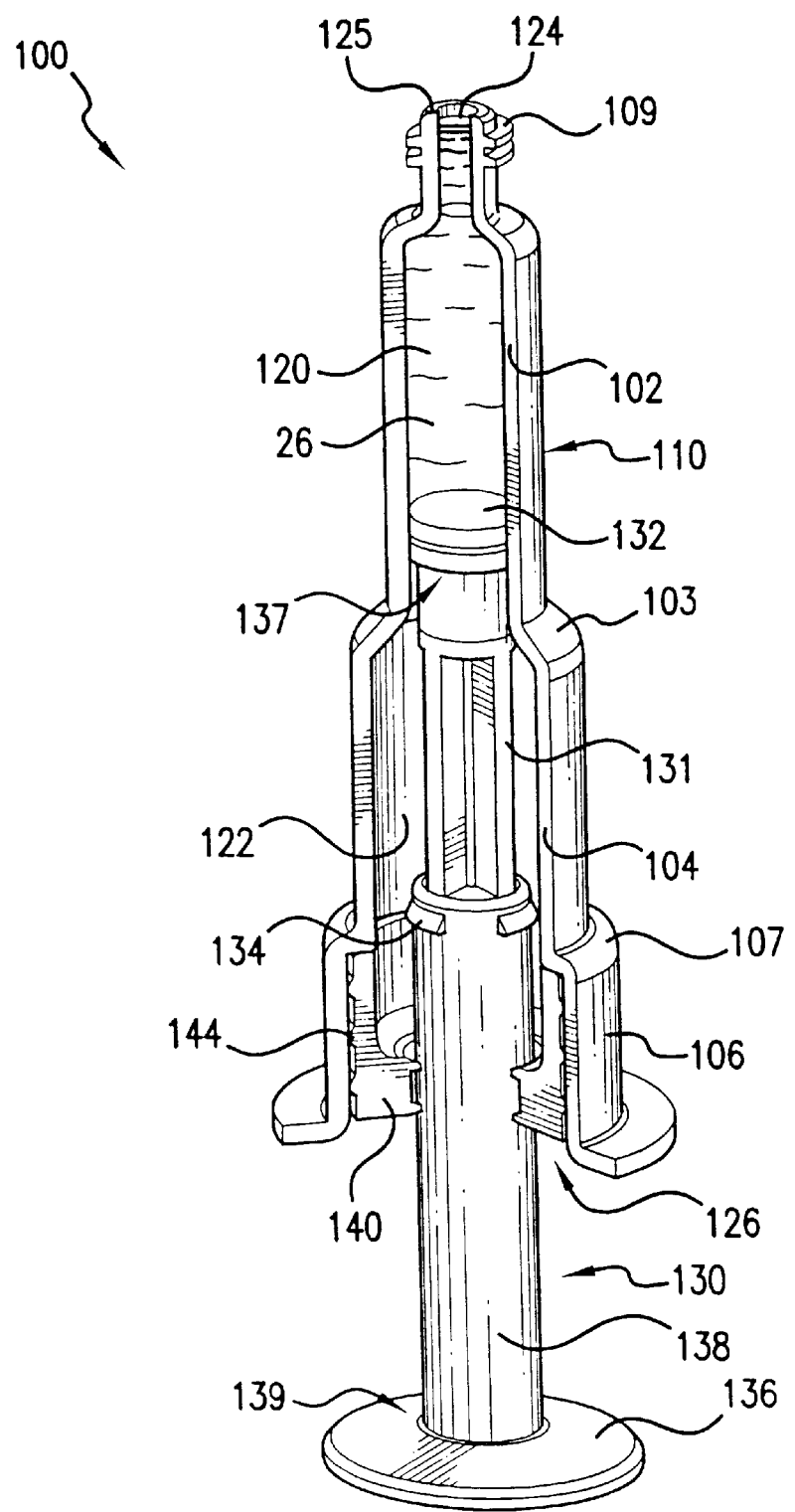
FIG. 6 is a sectional view of the syringe device of FIG. 5, where the plunger has been pushed into the top compartment for dispensing the mixed medicament, which is now in the top compartment, and the cap has been removed from the top-end opening.
Figure 7:
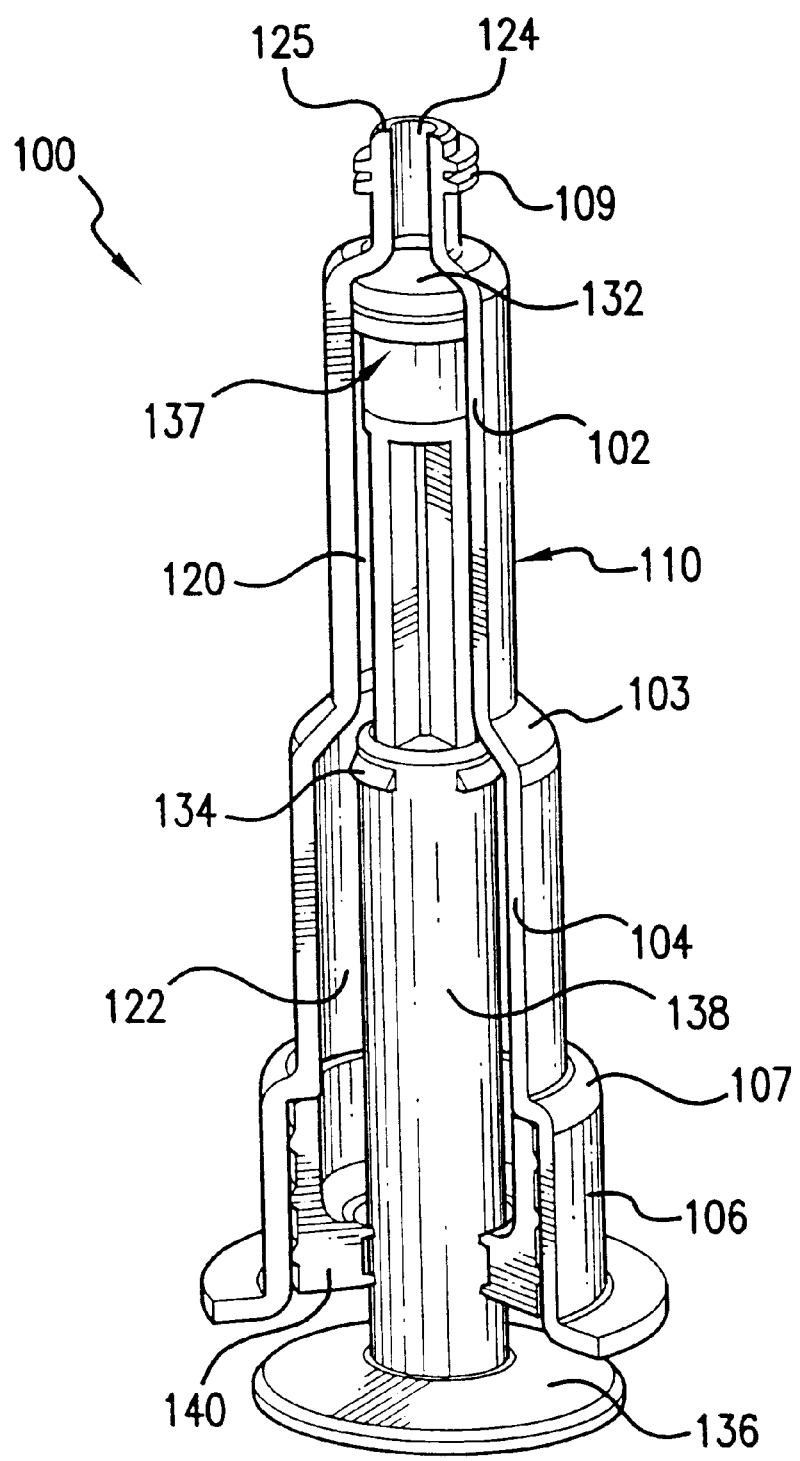
FIG. 7 is a sectional view of the syringe device of FIG. 6, where the plunger is in a fully depressed position after the medicament in the top compartment has been completely dispensed.

The process involved in preparing and dispensing the medicament from the two components stored in the syringe device 100 will now be described with references to FIGS. 5–7. In order to mix the two components of a medicament stored in the syringe device 100, the plunger 130 is first withdrawn towards the proximal end 139 of the plunger 130 so that the plunger head 132 disengages from the top-compartment sidewall 102 as illustrated in FIG. 5. During this procedure, the bung 140 remains in place within the base-skirt portion 106 in its sealed position. This is possible because the bung 140 is configured such that the static frictional force present at the bung to base-skirt-portion interface is greater than the static frictional force present at the bung to the plunger-shaft interface, allowing the plunger 130 to be withdrawn without displacing the bung 140 from its sealed position within the base-skirt portion 106. By withdrawing the plunger head 132 from the top-compartment sidewall 102, the two compartments are now in communication with one another so that the contents of the two compartments can mix.

During this operation, the withdrawal of the plunger 130 is limited by stopper tab 134 on the plunger shaft 138. As the plunger 130 is withdrawn further, the stopper tab 134 will touch the bung 140 and limit the travel of the plunger 130 so that a substantial portion of the plunger shaft 138 remains within the bottom compartment 122. Typically, the syringe device 100 would be shaken vigorously to mix the contents of the syringe device 100. And the presence of the substantial portion of the plunger shaft 138 inside the bottom compartment 122 enhances the mixing of the contents by functioning as an agitator during the shaking. This agitating function of the plunger shaft 138 may be further enhanced by providing vanes 131 in the portion of the plunger shaft that is positioned within the bottom compartment 122.

In the embodiment of the syringe where the bottom compartment is pre-filled using the lyophilization process, the disengaging the plunger head 132 from the top-compartment sidewall 102 may be accomplished by an alternative method. In this alternative method, the user simply unseals the top-end opening 124 of the syringe device 100 by unscrewing the cap 150. In this embodiment, the lyophilization process creates a vacuum condition in the bottom compartment 122 and the vacuum in the bottom compartment 122 pulls on the plunger head 132. But because the top compartment 120 is filled with liquid and sealed air-tight the plunger head 132 is prevented from being sucked into the bottom compartment 122.

Then, when the cap 150 is unscrewed from the top-end opening 124, the pressure inside the top compartment 120 will equalize with the atmospheric pressure and cause the plunger head 132 to be abruptly sucked into the bottom compartment 122 breaking the seal separating the two compartments. This abrupt breaking of the seal causes the liquid from the top compartment 120 to gush into the bottom compartment 122 enhancing the mixing of the liquid and the dry contents of the bottom compartment 122.

Once the contents of the syringe device 100 are completely mixed and the medicament is ready for dispensing, the syringe device 100 is oriented so that the top compartment is pointing downward. This will cause the medicament to drain into the top compartment 120. The volume of the two components of the medicament preferably is controlled so that the mixed medicament would fit completely inside the top compartment 120 without overflowing into the bottom compartment 122. This minimizes any portion of the medicament from being wasted.

Next, while maintaining the top compartment-down orientation of the syringe device 100, the plunger 130 is pushed down until the plunger head 132 sealingly engages the top-compartment sidewall 102. The syringe device 100 then may be turned so that the top end of the syringe device 100 points upwardly. Then, as shown in FIG. 6, the cap 150 may be removed and a syringe needle (not shown) may be attached to the top-end opening 124. Depending on the application, other dispensing apparatus may be attached to the top-end opening to dispense the medicament. In this configuration, the syringe device 100 operates like a standard syringe. To completely dispense the medicament contained in the top compartment 120, the plunger 130 is fully depressed into the syringe device 100 as illustrated in FIG. 7.

Figure 8:
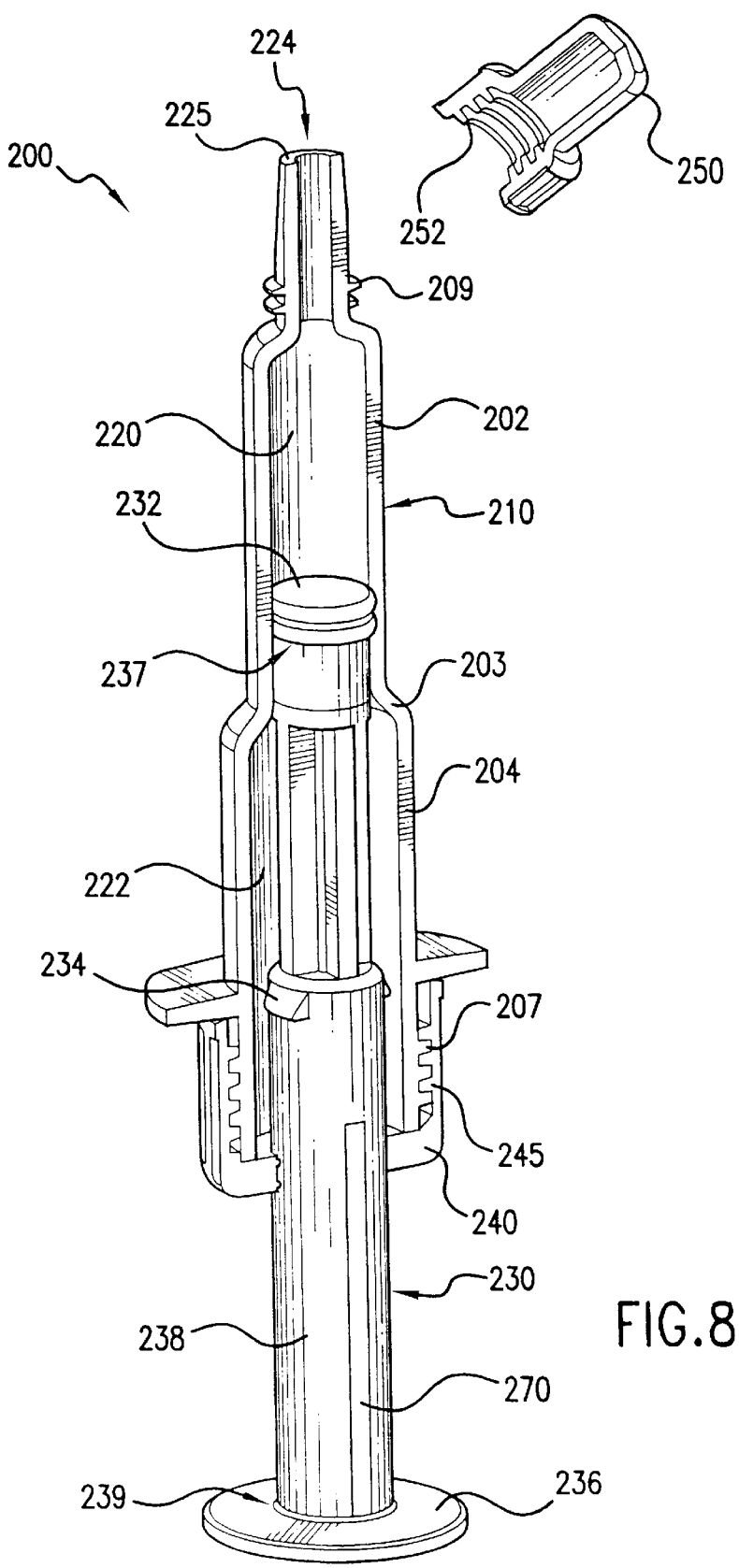
FIG. 8 is a sectional view of another two-compartment embodiment of the invention.

FIG. 8 illustrates another embodiment of a two-compartment syringe device where the bottom opening of the syringe body is sealed with a screw-type closure member. A two-compartment syringe device 200 comprises a syringe body 210 having a circular cross-section and openings at top and bottom ends. The syringe body 210 comprises a top-compartment sidewall 202 having one diameter and a bottom-compartment sidewall 204 having a larger diameter.

The syringe device 200 further comprises a plunger 230 having a plunger head 232 at its distal end 237. When the plunger 230 is inserted inside the syringe body 210, the plunger head 232 sealingly engages the top-compartment sidewall 202 and divides the inside of the syringe body 210 into a top compartment 220 and a bottom compartment 222.

Figure 9:
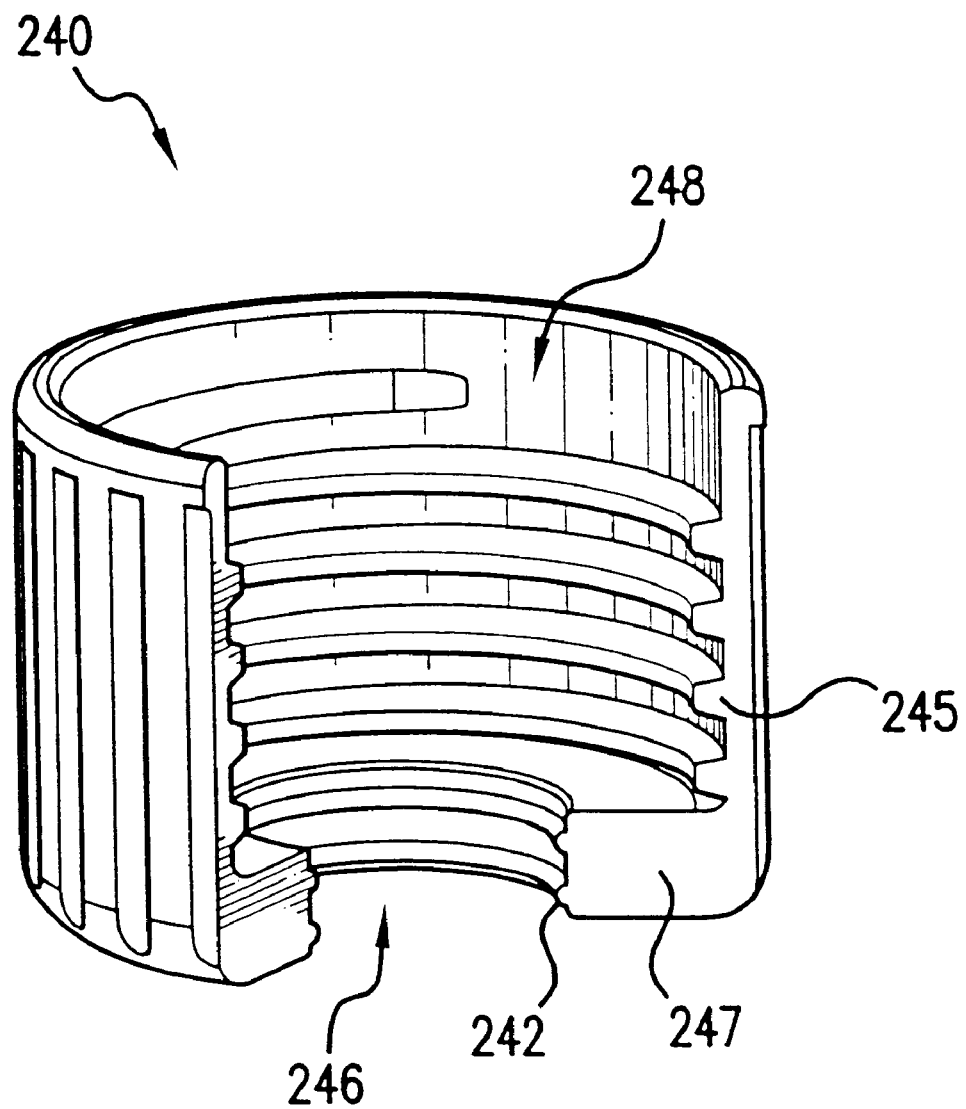
FIG. 9 is a sectional view of the bottom closure member from the syringe device of FIG. 8.

A bottom closure member 240 is also provided that is slidably mounted on the plunger 230 and is movable along plunger shaft 238 between the plunger's proximal end 239 and stopper tabs 234. The bottom closure member 240 is illustrated in detail in FIG. 9. The bottom closure member 240 further comprises a base portion 247 and a well portion 248.

The base portion 247 has a central aperture 246 for slidably receiving the plunger shaft 238. The sidewall of the central aperture 246 is configured with at least one sealing ribs 242 so that an appropriate seal is maintained at the interface between the plunger shaft 238 and the bottom closure member 240.

The well portion 248 is sized to receive the bottom end of the syringe body 210 and is provided with screw threads 245 along its inside wall. The syringe body 210 is provided with mating screw threads 207 near its bottom end so that the bottom closure member 240 can be screwed onto the syringe body 210 and seal the bottom opening of the syringe body 210 as illustrated in FIG. 8. The bottom closure member 240 may be made of a single material or formed as a composite, but preferably at least the sealing ribs 242 and the inside surface of the base portion 247 that sealingly engages the syringe body 210 are made from an elastomer.

Top-end opening 224 of the syringe body 210 is preferably sealed with a removable closure. In this embodiment, the top-end opening 224 is sealed with a screw cap 250. The screw cap is provided with screw threads 252 and the syringe body 210 is provided with mating threads 209 so that the screw cap 250 can be screwed onto the syringe body 210.

The desired quality of the seals produced by the screw cap 250 and the bottom closure member 240 will be dictated by the particular application for the syringe device such as the particular substance stored in each compartment of the syringe. For example, the seals may be hermetic or non-hermetic but liquid tight.

Alternatively, the top-end opening 224 may be sealed with any other appropriate sealing methods. For example, the top-end opening 224 may be heat sealed along the rim 225 with a foil membrane made of an appropriate material that can be peeled away to dispense the contents of the syringe.

Figure 10:
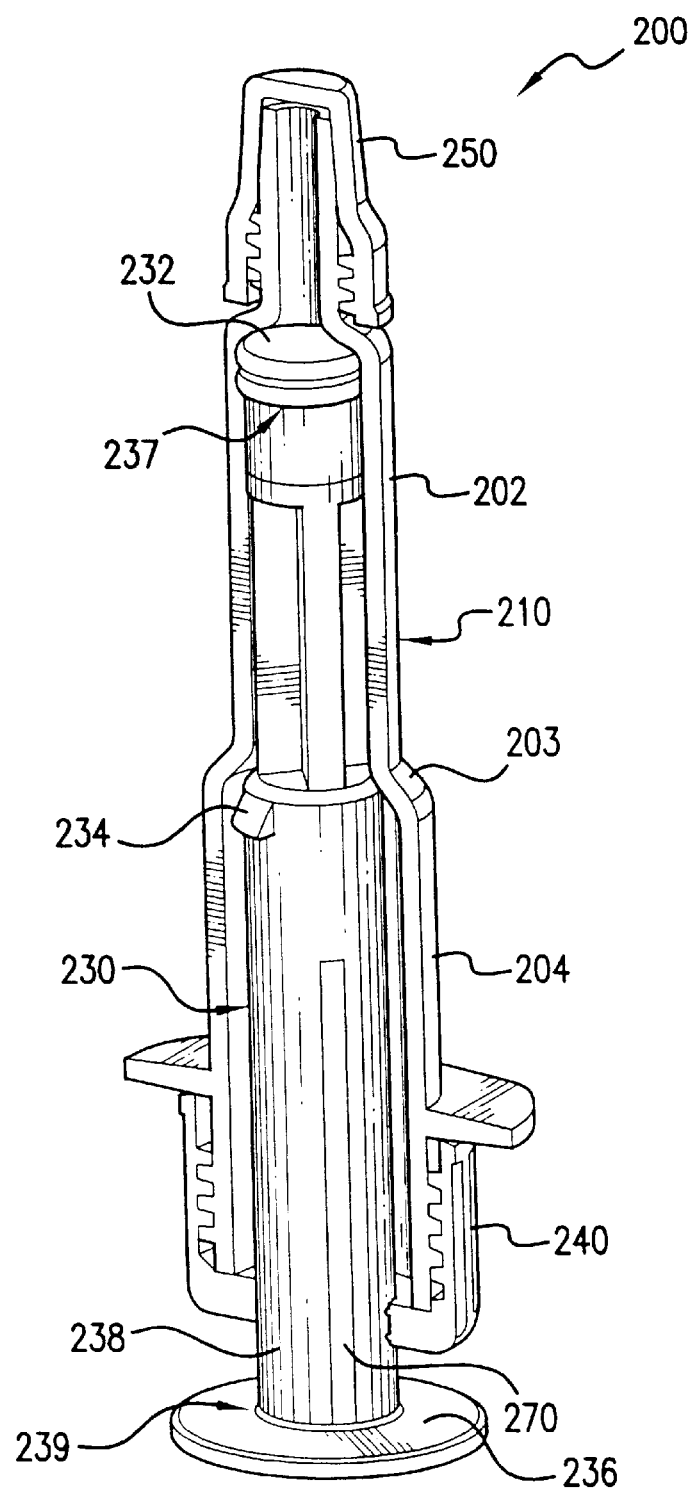
FIG. 10 is a sectional view of the syringe device of FIG. 8 before it is filled with its contents.

FIG. 10 illustrates the syringe device 210 in a state before each of its two compartments are filled with components of a medicament. The plunger 230 is fully inserted into the syringe body 210. The bottom closure member 240 is fully screwed into position closing the bottom end of the syringe body 210. The screw cap 250 is screwed on to the top end of the syringe body 210 sealing the top-end opening 224 to prevent any contaminants from entering the syringe. In fact, all components of the syringe device 200 are preferably provided in sterile condition to prevent any contamination of the medicament or formulation to be stored in the syringe device 200. Of course, if required, the filling and assembly operation itself may be conducted in a sterile environment.

Figure 11:
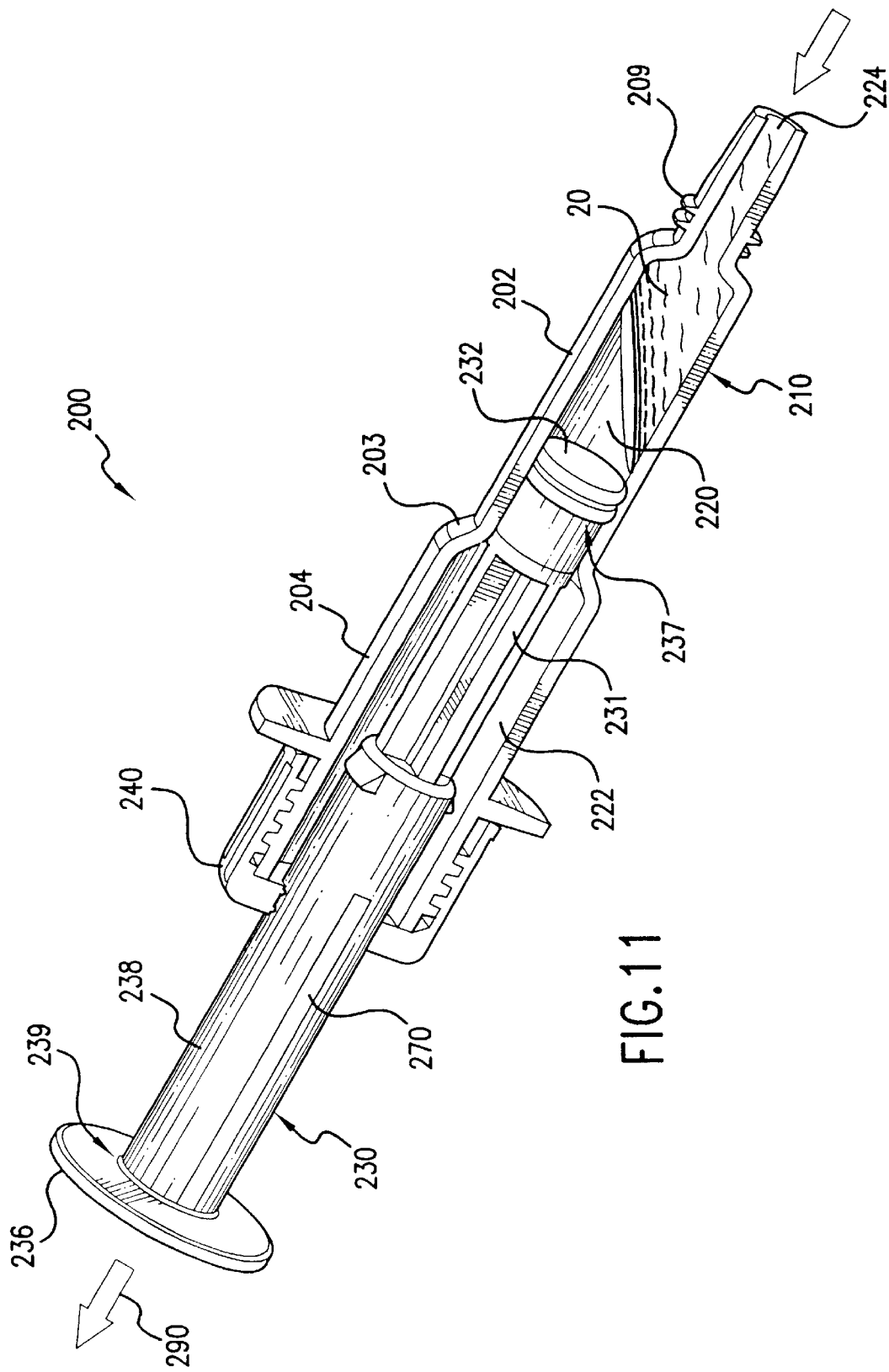
FIG. 11 is a sectional view of the syringe device of FIG. 8 in an interim stage in the process of filling and assembling the syringe where the top compartment is being filled a first component of a formulation.

Next, FIGS. 11–17 will be utilized to illustrate the process involved in filling the syringe device 200 for storage and also mixing the contents of the syringe device 200 and preparing to dispense the mixed formulation. In this example, the top compartment 220 will be filled before the bottom compartment 222. In FIG. 11, the first component 20 being introduced into the top compartment 220 is a liquid. The screw cap 250 is removed from the syringe body 210. While the top opening 224 of the syringe device is submerged in the liquid substance 20, plunger 230 is withdrawn from a fully inserted position in the direction of the arrow 290. The vacuum created in the top compartment 220 by this motion will draw the liquid substance 20 into the top compartment 220.

The plunger 230 may be provided with a thumb rest 236 near the proximal end 239 of the plunger shaft 238 that can also be used to withdraw the plunger 230 from the syringe body 210. Such thumb rest 236 will be useful also when pressing the plunger 230 into the syringe body 210. If desired, the plunger 230 may be positioned at its sealed position at the bottom end of the top-compartment sidewall portion 202 and then filled through the top opening. The top compartment 220 maybe filled with either a liquid or a powder substance.

In FIG. 11, the bottom closure member 240 is illustrated as being in its sealed position sealingly engaged to the syringe body 210 while the top compartment 220 is being filled. However, the bottom closure member 240 may just as easily be unscrewed from the syringe body 210 during this process.

Figure 12:
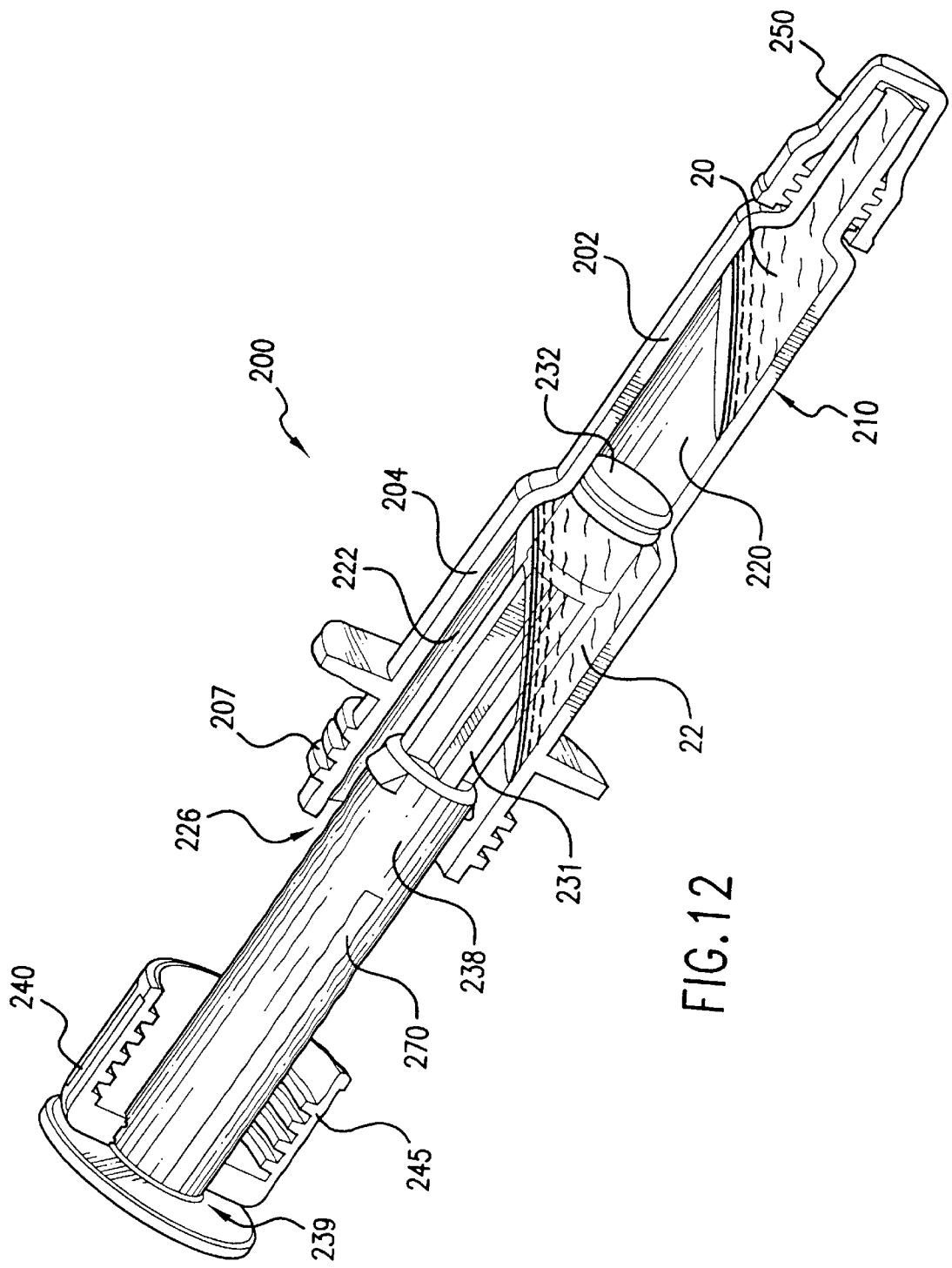
FIG. 12 is a sectional view of the syringe device of FIG. 11 in a next interim stage in the process of filling and assembling the syringe device where the bottom compartment is being filled with a second component of the formulation.

FIG. 12 illustrates the next stage in the filling process. After the top-compartment 220 is filled with a desired amount of the first component 20 of a medicament, the top opening 224 is sealed with a screw cap 250. The bottom closure member 240 is then unscrewed from the syringe body 210 to its unsealed position (if not already in its unsealed position) removed. Next, the bottom compartment 222 is filled with a second component 22 of a medicament through the bottom opening 226. During this process, the plunger 230 is maintained in its position so that the plunger head 232 remains engaged with the top-compartment sidewall 202 confining the first component 20 within the top compartment 220 and the bottom closure member 240 is positioned near the proximal end 239 of the plunger 230 to facilitate the filling of the bottom compartment 222.

Figure 13:
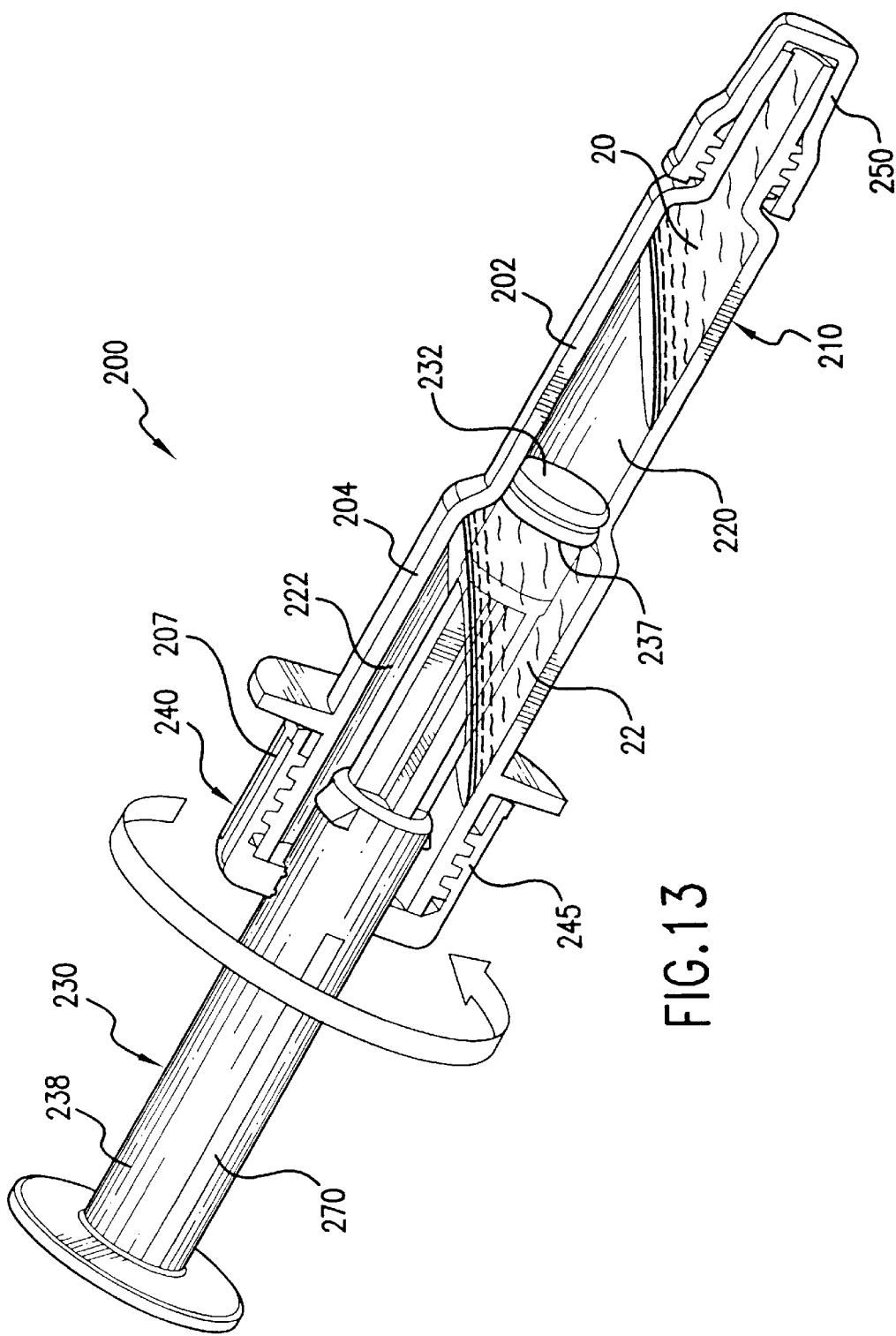
FIG. 13 is a sectional view of the syringe device of FIG. 12 in a next stage in the process of filling and assembling the syringe device where the two compartments have been filled and sealed.

After a desired amount of the second component 22 is introduced into the bottom compartment 222, the bottom opening 226 is sealed by sliding the bottom closure member 240 along the plunger shaft 238 towards its distal end 237 and screwing the bottom closure member 240 onto the syringe body 210. FIG. 13 illustrates the syringe device 200 after the bottom closure member 240 has been screwed into its sealed position. The two components 20, 22 are kept separate in their respective compartments 220, 222 within the syringe device 200 and they may be stored until ready to be mixed and dispensed.

Figure 14:
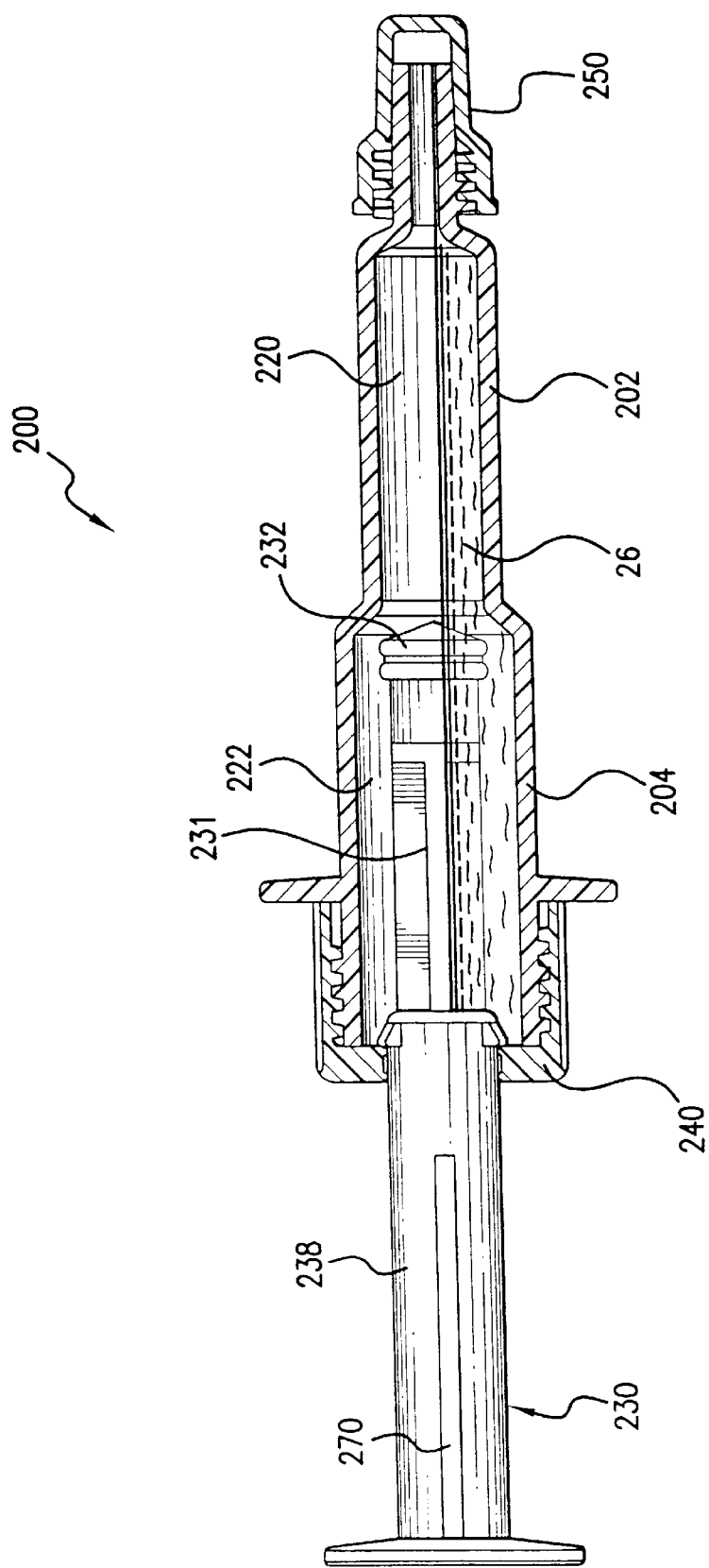
FIG. 14 is a sectional view of the syringe device of FIG. 13 where the partition between the two compartments has been unsealed and the first and second components are being mixed.

FIG. 14 illustrates the syringe device 200 in a configuration where the two components 20, 22 are being mixed into a medicament or a formulation. The plunger 230 has been withdrawn so that the plunger head 232 is no longer sealingly engaging the top-compartment sidewall 202 but lies within the bottom-compartment 220. The plunger 230 may be provided with stopper tabs 234 that limit the travel of the plunger 230 when it is being withdrawn to prevent any compromise of the seal between the plunger shaft 238 and the bottom closure member 240. Because the bottom-compartment sidewall 204 has a larger diameter than the plunger head 232, the top and bottom compartments 220, 222 are in flow communication with one another. So that the two components 20, 22 may mix. The user may shake the syringe device 200 to properly combine the two components 20, 22. The presence of the plunger 230 inside the bottom compartment 222 acts as an agitator during the shaking operation and facilitate the mixing of the components. The portion of the plunger 230 that lies within the bottom compartment 222 may be configured with vanes 231 that enhances the agitating function of the plunger 230.

Figure 15:
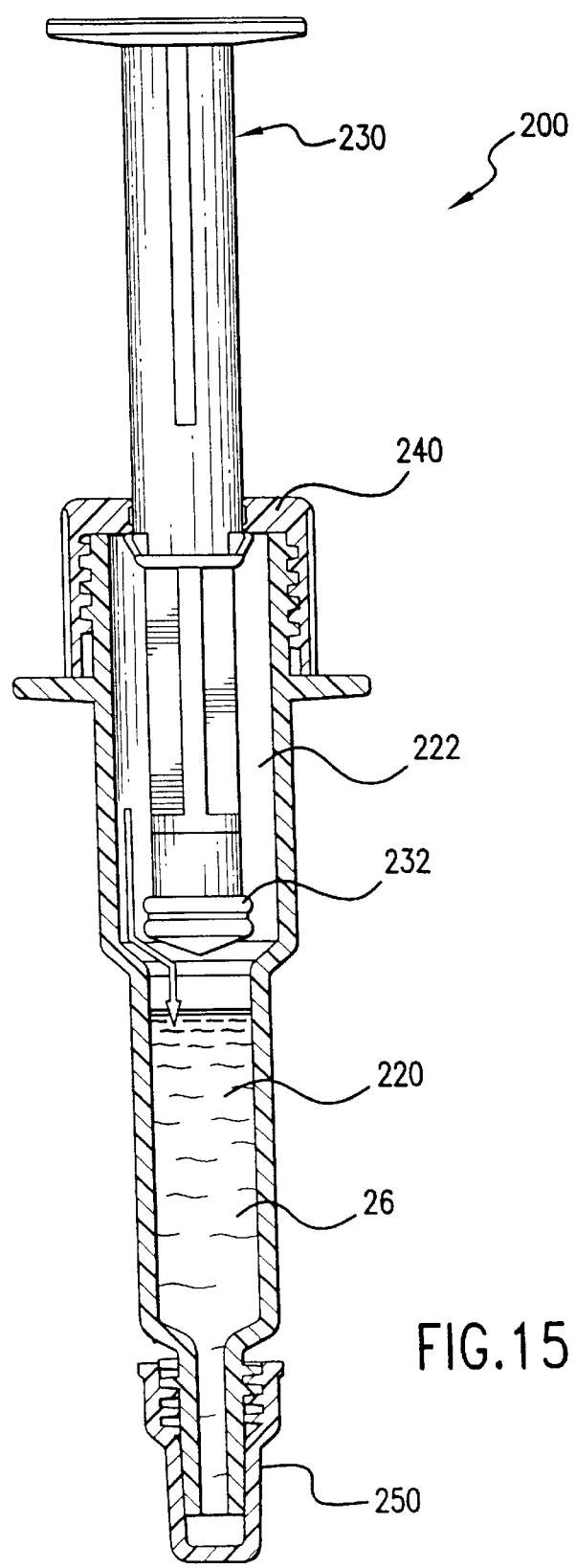
FIG. 15 is a sectional view of the syringe device of FIG. 14 in a next stage in the process of mixing and dispensing the contents of the syringe device.
Figure 16:
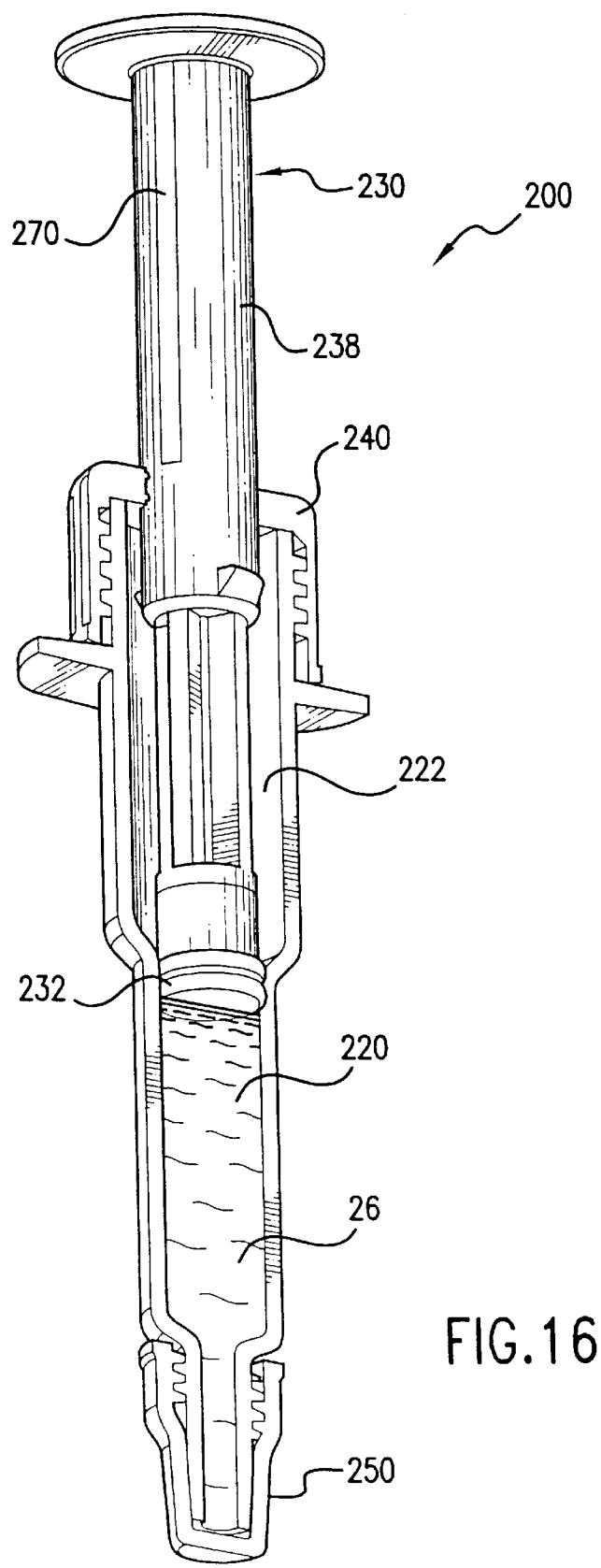
FIG. 16 is a sectional view of the syringe device of FIG. 15 in a next stage in the process of mixing and dispensing the contents of the syringe device ready for dispensing.
Figure 17:
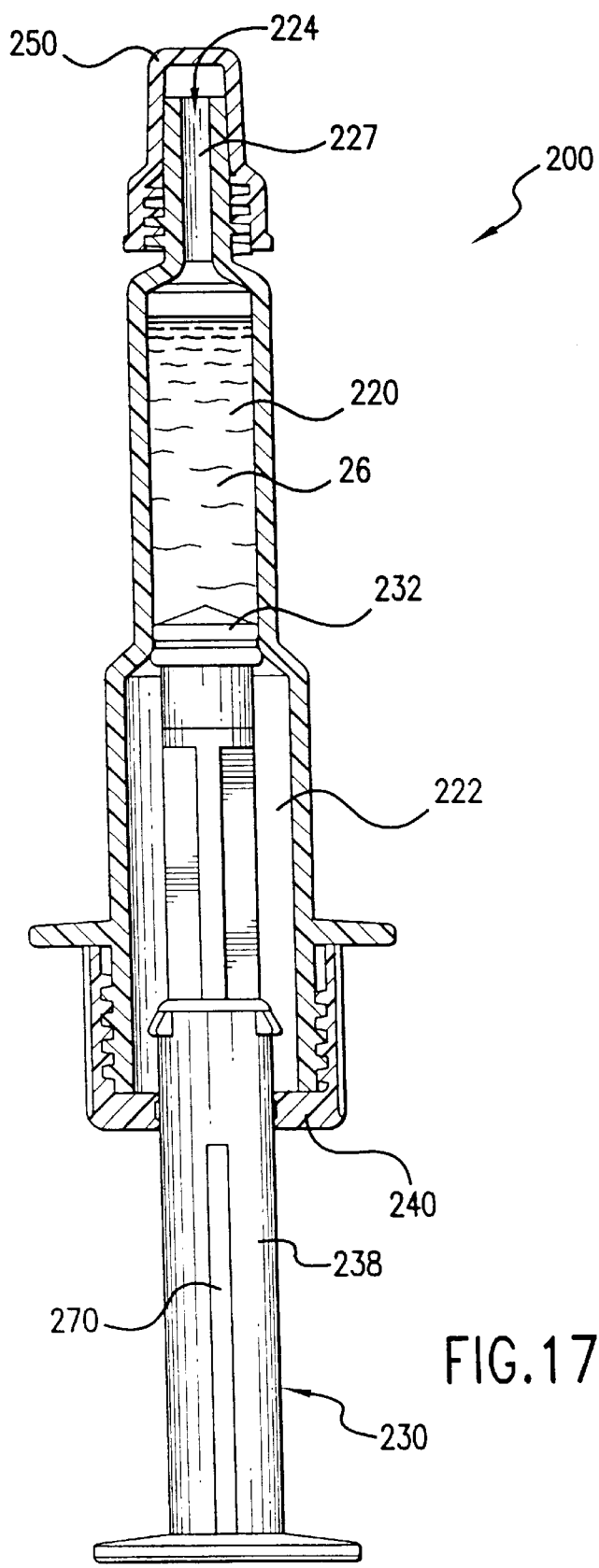
FIG. 17 is a sectional view of the syringe device of FIG. 16 in a different orientation.

To dispense the medicament, the syringe device 200 is placed in an orientation illustrated in FIG. 15 with its top end pointing down and the plunger end pointing up. This causes the medicament 26 to drain into the top compartment 220. The plunger head 232 is then pushed back into the top compartment 220, as illustrated in FIG. 16, and the syringe device 200 may be used like a standard syringe. The user would place the syringe device 200 in a top end up orientation as illustrated in FIG. 17. Any air trapped in the top compartment 220 would then rise to form the head space 227. The screw cap 250 may then be removed to attach an appropriate dispensing device to the top end of the syringe device 200. For example, a hypodermic needle may be attached to the syringe device 200 at the top end.

Once an appropriate dispensing device is attached, the plunger 230 is pressed further into the syringe body. But as the plunger head 232 advances further into the top compartment 220, the increase in the volume of the bottom compartment 222 will create a low pressure condition in the bottom compartment 222 and may interfere with the dispensing process. To alleviate this concern, an air vent channel 270 may be provided on the plunger shaft 238. As the plunger advances further into the syringe body 210 the air vent channel 270 will break the seal between the bottom closure member 240 and the plunger shaft 238 and allow outside air to vent into the bottom compartment 222. Similarly, in the illustration of FIG. 11, the air vent channel 270 will prevent any excessive air pressure build up in the bottom compartment 222 as the plunger 230 is being withdrawn to fill the top compartment 220.

In an alternate embodiment, the bung 140 and the syringe body 110 of the syringe device 100 illustrated in FIG. 1 may be configured and adapted so that the bung 140 may be screwed into the syringe body 110. The bung 140 may be provided with screw threads on its outer surface and the inside wall of the syringe's base-skirt portion 106 may be provided with mating screw threads.

Figure 18:
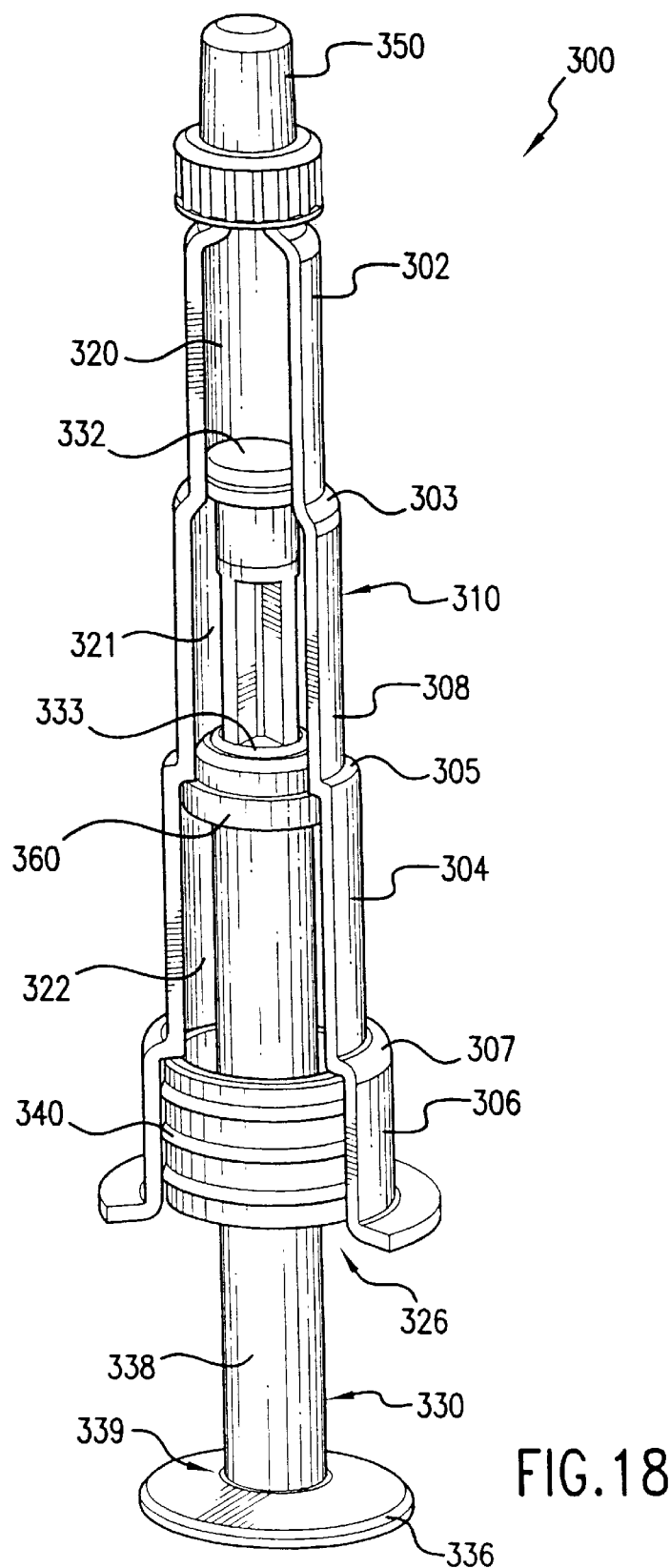
FIG. 18 is a perspective view of another embodiment of the invention in the form of a three-compartment syringe where the syringe body is illustrated as being translucent in order to show the internal structures of the syringe.

FIGS. 18–26 illustrate another embodiment of the invention, a syringe device 300 having three compartments for storing three different components of a medicament or a formulation, each in separate compartments until ready for use, wherein the three components may be mixed to form the medicament. FIG. 18 is an illustration of the fully assembled syringe device 300 in a ready-for-storage configuration. Plunger 330 is positioned inside a syringe body 310 so that plunger head 332 sealingly engages top-compartment sidewall 302, in proximity to shoulder 303, and a first bung 360 is sealingly engaged with middle ridge 305. In this storage configuration, the plunger head 332 forms the partition between top compartment 320 and middle compartment 321. The first bung 360 forms the partition between middle compartment 321 and bottom compartment 322. The seal formed by the plunger head 332 and the top-compartment sidewall 302 is hermetic so that components stored in the top compartment 320 and the middle compartment 321 may be kept separate until ready to be mixed. The seal formed by the first bung 360 and the middle ridge 305 serves the same function between the middle compartment 321 and bottom compartment 322.

Figure 19:
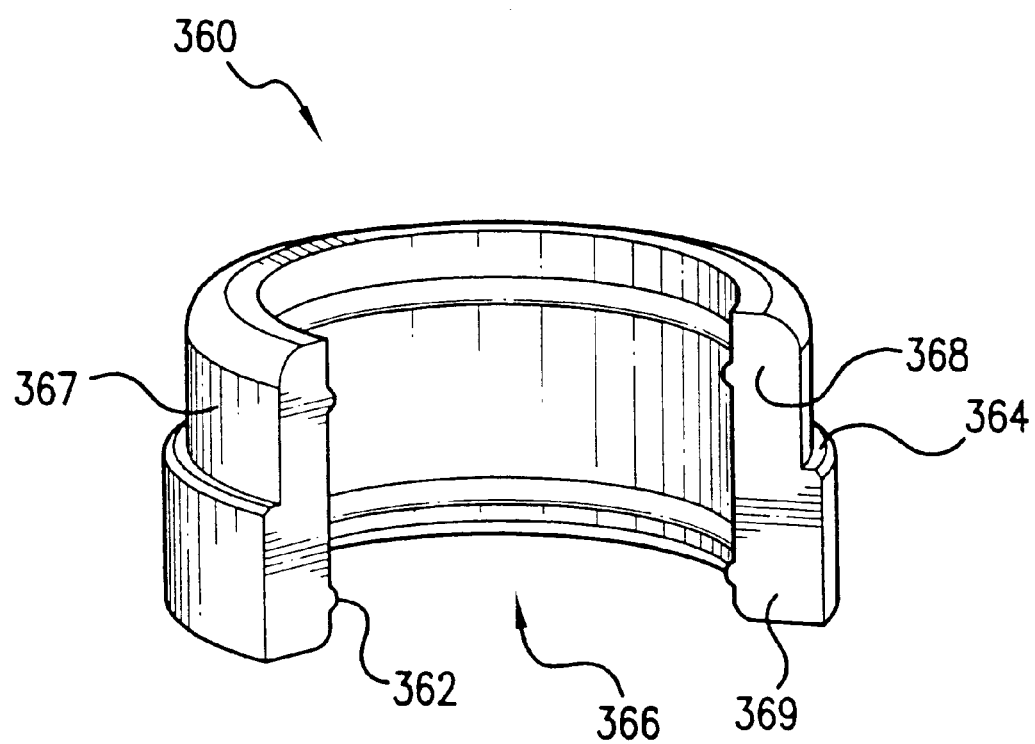
FIG. 19 is a sectional view of the first bung of the syringe device of FIG. 18.

FIG. 19 illustrates a cross-sectional view of the first bung 360. The first bung 360 is provided with a central aperture 366 through its center so that the plunger 330 is received through the central aperture and the first bung 360 can be moved up and down the plunger shaft 338. The sidewall of the central aperture 366 may be provided with a plurality of inner sealing ribs 362 for sealingly engaging the plunger shaft 338. Top portion 368 of the first bung 360 has a smaller outer diameter than the bung's bottom portion 369. The outer diameter of the top portion 368 is such that the top portion 368 fits within the middle-compartment sidewall 308 and sealingly engages the middle-compartment sidewall 308. Otherwise the outer surface 367 fits snugly to form a seal.

The bottom portion 369 has a larger diameter than the top portion 368 so that a stopper ridge 364, separating the top portion from the bottom portion 369, interferes with the middle ridge 305 of the syringe body 310, preventing the first bung 360 from traveling too far into the middle compartment 321. But the diameter of the bottom portion 369 is sufficiently small that it does not contact the bottom-compartment sidewall 304 and leaves a sufficient clearance space between the bottom-compartment sidewall 304 and the bottom portion 369 for the contents of the syringe device 300 to pass through the space when the first bung 360 is dislodged to its unsealed position.

The first bung 360 is preferably made from an elastomer and the diameter of the top portion 368 of the first bung 360 is such that when the first bung 360 is in its sealed position, the top portion 368 compressively seals against the inside surface of middle-compartment sidewall 308. If desired, a plurality of outer sealing ribs (not shown) may be provided along the outer surface 367 of the top portion 368 to facilitate the sealing. Alternatively, the first bung 360 may have a composite structure where at least the seal forming portions, i.e., the sealing ribs 362 and the top portion 368, are made from one or more elastomers. The rest of the first bung 360 may be made from any material suitable to maintain the structural shape of the first bung 360 and chemically compatible with the elastomer portions. Bottom portion 369 of the first bung 360 has a smaller diameter than the bottom-compartment sidewall 304 so that the first bung can be moved through the bottom compartment 322 to form a seal with the inside surface of the middle-compartment sidewall 308.

A second bung 340 is positioned within the base-skirt portion 306, of the syringe housing 310 sealing the bottom-end opening 326. The second bung 340 presses up against base ridge 307 which functions as a stopper preventing the bung 340 from traveling too far into the syringe body 310.

Figure 20:
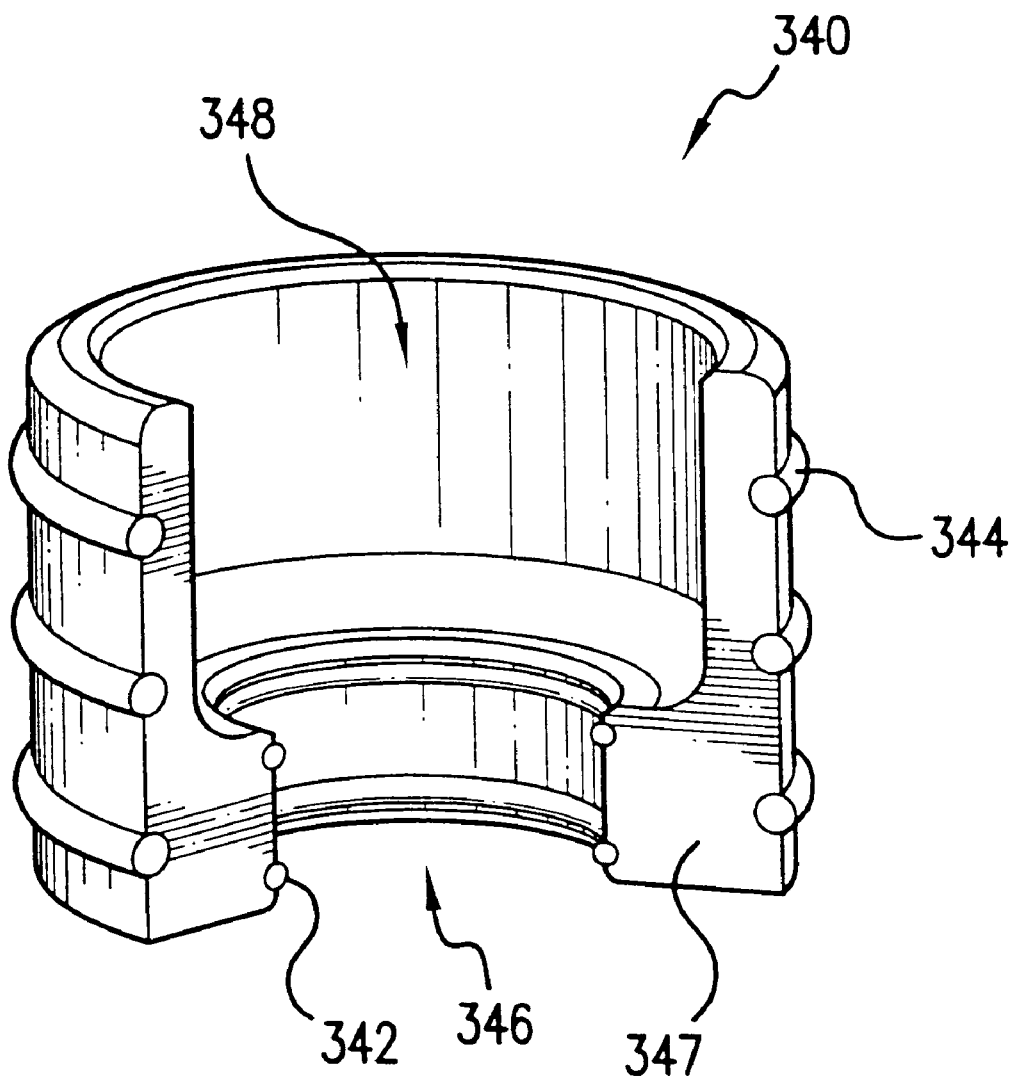
FIG. 20 is a sectional view of the second bung of the syringe device of FIG. 18.

A detailed cross-sectional view of the second bung 340 is illustrated in FIG. 20. The second bung 340 is similar in structure as the bung 340 of the syringe device 100, illustrated in FIG. 2. The second bung 340 has a central aperture 346 through its axial center so that the plunger 330 can be received through the central aperture and the second bung 140 can slide up and down the plunger shaft 338. The outer surface of the second bung 340 is provided with a plurality of outer sealing ribs 344 for sealingly engaging the inside surface of the base-skirt portion 306 and forming a hermetic seal at the bottom-end opening 326. The side wall of the central aperture 346 is provided with a plurality of inner sealing ribs 342 for sealingly engaging the plunger shaft 338. The diameters of the outer surface and the central aperture 346 of the second bung 340 is sized so that the sealing ribs may form hermetic seals with the mating surfaces through compression.

The second bung 340 also may be provided with a well 348 so that only the lower portion 347 of the bung 340 forms the seal with the plunger shaft 338. As discussed with reference to the bung 140, illustrated in FIG. 2 above, the inner sealing ribs 342 and the outer sealing ribs 344 of the second bung 340 are preferably configured so that the plunger 330 can be partially withdrawn form the syringe body 310 without dislodging the second bung 340 from its sealed position within the base-skirt portion 306. The top-end opening 324 (see FIG. 18) is sealed with a cap 350 which is configured to be removed when the contents of the syringe device 300 has been mixed and is ready to be dispensed.

The process of assembling and filling the syringe device 300 according to the invention will now be described with references to FIGS. 21–23. A syringe body 310 is oriented in an upright position with its top-end opening 324 pointing upwardly. A plunger 330 is first inserted through bottom-end opening 326 and into the syringe body 310 plunger head 332 first until the plunger head 332 engages the top-compartment sidewall 302. The engagement of the plunger head 332 with the top-compartment sidewall 302 forms a hermetic seal at the bottom of the top compartment 320 in proximity to the shoulder 303. The first bung 360, in this assembly configuration, is positioned between the middle compartment 321 and the bottom compartment 322.

The top compartment 320 is then filled with a first component of a medicament through the top-end opening 324 and sealed with a cap 350. In this embodiment of the invention, the first component is preferably the liquid component of the medicament. To prevent any degradation of the first component from prolonged exposure to air during storage, the top compartment 320 is filled completely with the first component liquid, minimizing or eliminating any air pockets inside the top compartment 320 when it is sealed with the cap 350. In the alternative, the filling process may be conducted under a vacuum or an inert gas environment so that even if the top compartment is not filled completely with the first component liquid, there would not be any air trapped inside the top compartment after being sealed with the cap 350.

The top compartment may also be filled by inserting the plunger completely to the end of the top compartment, immersing the open top end in the first component liquid, then sucking the liquid into the top compartment by pulling the plunger back to the sealed position between the compartments.

As discussed above in reference to the cap 150 of the syringe device 100, the cap 350 is preferably configured and adapted to form a hermetic seal around the top-end opening 324. And the particular requirement for the quality of the seal formed by the cap at the top-end opening and the seals formed between the compartments throughout the syringe device 300 would be dictated by the particular application for which the syringe device is intended.

Figure 21:
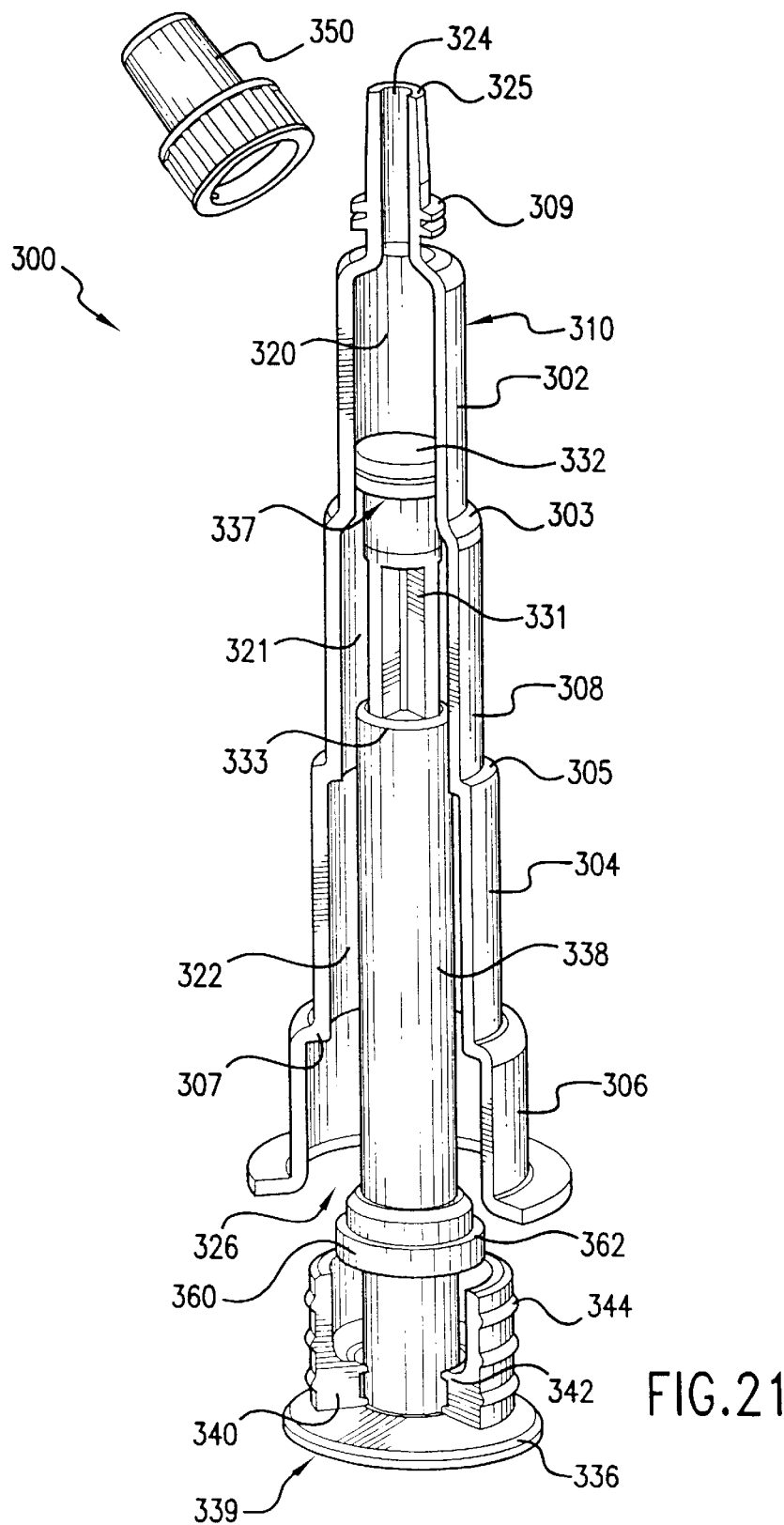
FIG. 21 is a sectional view of the syringe device of FIG. 18, illustrating the syringe device in an interim stage in the process of filling and assembling the syringe device where the plunger is inserted into the syringe body so that the plunger head is sealingly engaged with the top-compartment sidewall.
Figure 22:
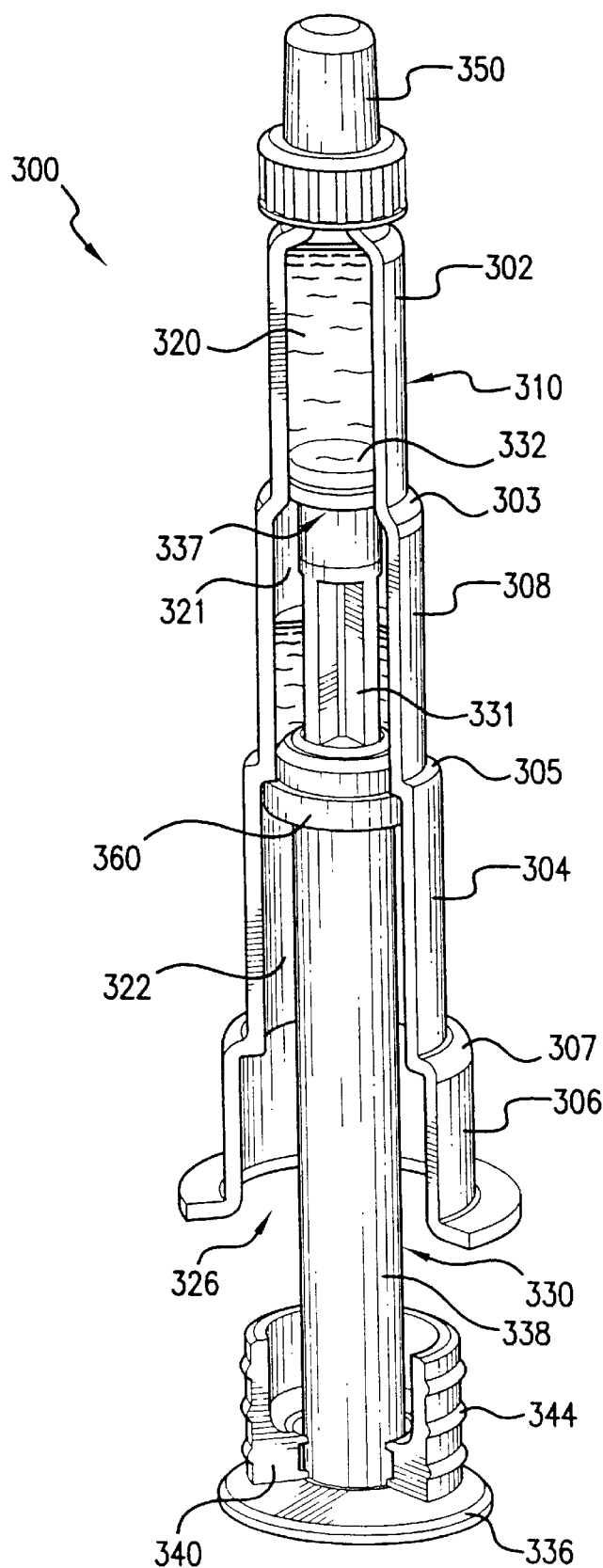
FIG. 22 is a sectional view of the syringe device of FIG. 21, illustrating the syringe device in an interim stage in the process of filling and assembling the syringe device where its top and middle compartment has been filled and sealed.

FIG. 21 is a sectional illustration of the syringe device 300 at this stage of the assembly. The top compartment 320 has been filled with the component of a medicament and the top-end opening 324 is about to be sealed by the cap 350. After the cap 350 is in place, the syringe device 300 may be turned 180 degrees, with the capped end oriented downward, so that the middle compartment 321 and the bottom compartment 322 may be filled. At this stage of the assembly, the first bung 360 and the second bung 340 are positioned near the thumb rest 336 of the plunger 330, as illustrated in FIG. 21, so that bottom-end opening 326 is free of any encumbrances. The bungs are kept from sliding down the plunger shaft 338 by the static frictional forces between the bungs and the plunger shaft 338.

The middle compartment 321 is then filled with a second component of the medicament through the bottom-end opening 326. The second component may be a liquid or a powder substance but as discussed above, in reference to the filling process of the bottom compartment 122 of the syringe device 100 illustrated in FIGS. 1–3, the configuration of the syringe device 300 is particularly well suited for filling the middle compartment 321 using the lyophilization process. The second component of the medicament in a hydrated form would be placed inside the middle compartment 321. Then, the first bung 360 is moved down the plunger shaft 338 until it snugly fits into the middle compartment sidewall 308 so that the first bung 360 is not fully engaged into its sealed position. As illustrated in FIG. 22, during the lyophilization process, the vacuum created in the middle compartment 321 pulls the first bung 360 completely into the middle compartment 321 until the stopper ridge 364 of the first bung 360 comes in contact with middle ridge 305 of the syringe body 310. The first bung 360 thus forms a hermetic seal between the middle compartment 321 and the bottom compartment 322.

Next, the bottom compartment 322 is filled with a third component of the medicament through the bottom-end opening 326 and sealed with the second bung 340 also using the lyophilization process. Alternatively, the bottom compartment may not be filled using the lyophilization process, in which case, the second bung 340 and the syringe body 310 are configured and adapted to form a seal at the bottom opening 326 by mechanically pushing or screwing the second bung 340 into the sealed position. In these alternative embodiments, the plunger shaft 338 is provided with a venting channel, similar to the venting channel 370 of the device 300 illustrated in FIGS. 10–17, to relieve the pressure built inside the bottom compartment 322 during the sealing process.

Figure 23:
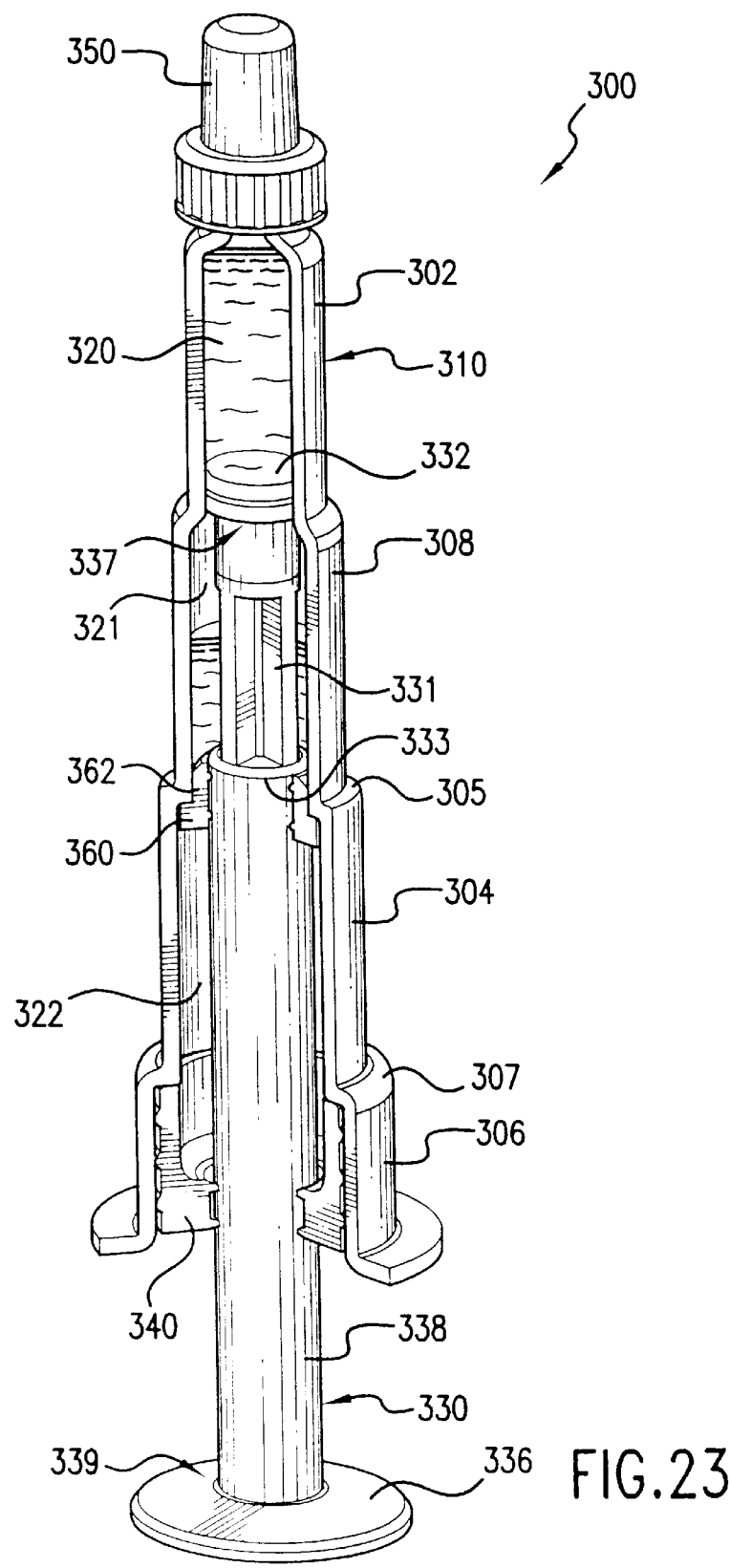
FIG. 23 is a sectional view of the syringe device of FIG. 22, illustrating the syringe device in a next interim stage in the process of filling and assembling the syringe device where the bottom compartment has been filled and sealed.

FIG. 23 illustrates the fully assembled syringe device 300 in the storage configuration. The syringe device 300 now consists of three completely sealed compartments—the top compartment 320, the middle compartment 321, and the bottom compartment 322—where each compartment is holding a component of a medicament for storage until ready to be mixed just prior to use.

Figure 24:
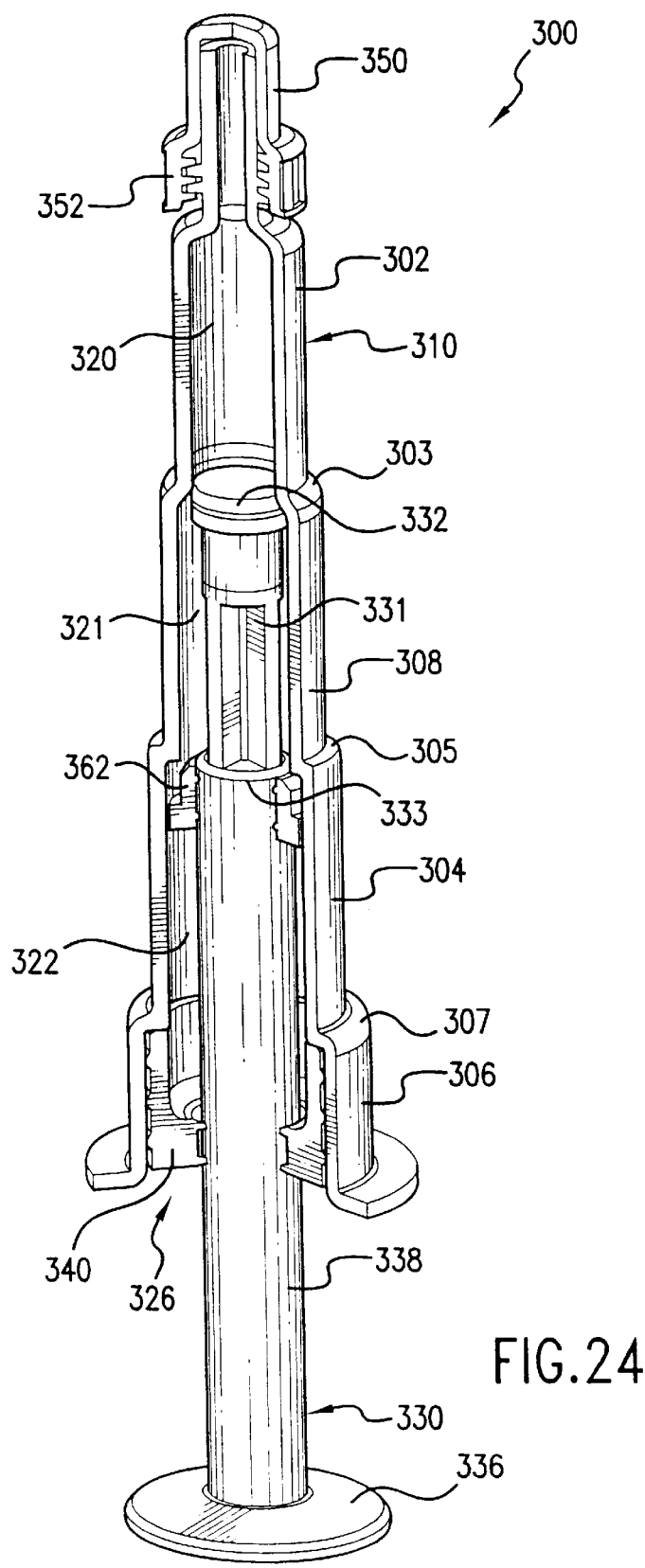
FIG. 24 is a sectional view of the syringe device of FIG. 23, where the plunger has been retracted so that the plunger head is in the middle compartment and the first bung is in the bottom compartment so that the three compartments are in communication with one another allowing the contents of the three compartments to mix.
Figure 25:
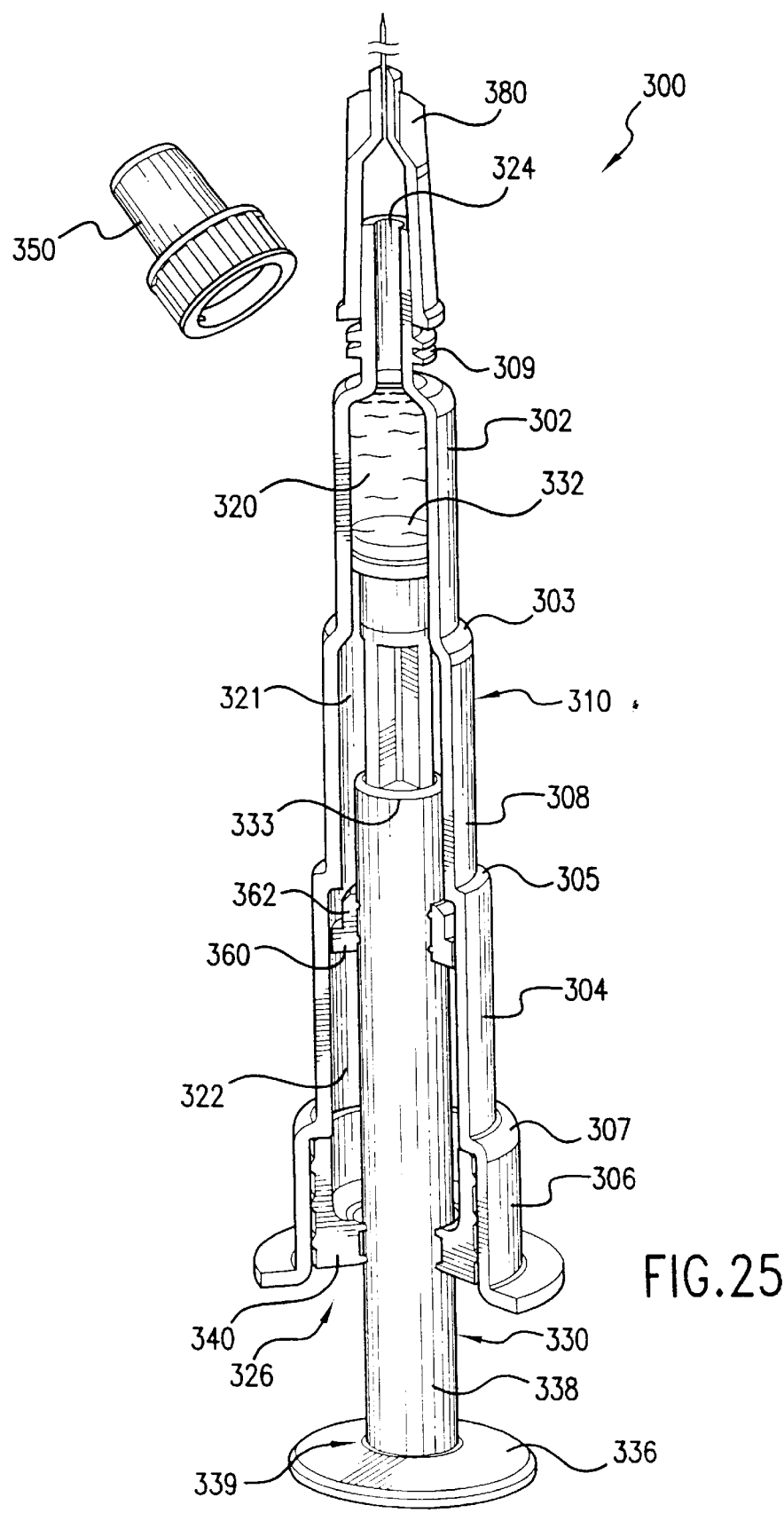
FIG. 25 is a sectional view of the syringe device of FIG. 24, where the plunger has been pushed into the top compartment for dispensing the mixed medicament, which is now in the top compartment, and the cap has been removed from the top-end opening.
Figure 26:
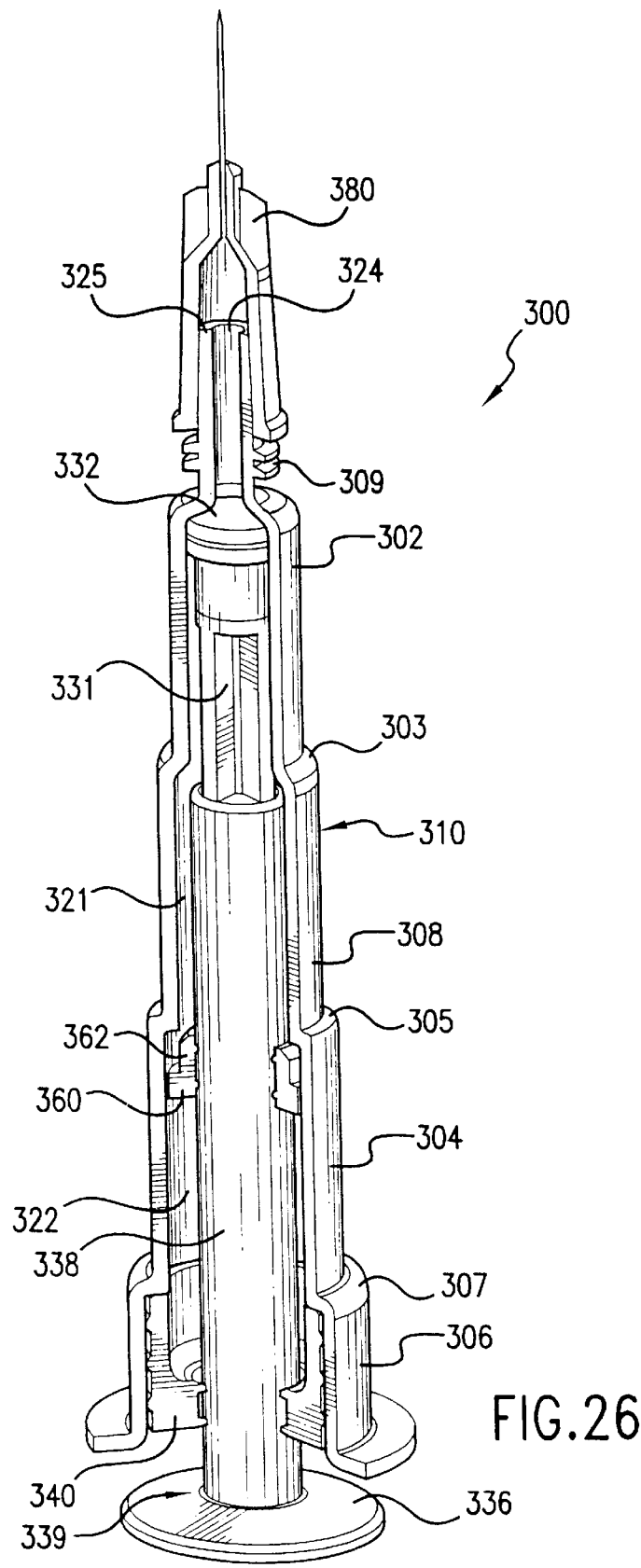
FIG. 26 is a sectional view of the syringe device of FIG. 25, where the plunger is in a fully depressed position after the medicament in the top compartment has been completely dispensed.

The process involved in preparing and dispensing the medicament stored in the syringe device 300 will now be described with references to FIGS. 24–26. In order to mix the three components stored in the syringe device 300, the plunger 330 is first pulled back towards the proximal end 339 of the plunger 330 so that the plunger head 332 disengages from the top-compartment sidewall 302 as illustrated in FIG. 24. The motion of disengaging the plunger head 332 from the top-compartment sidewall 302 simultaneously disengages the first bung 360 from its sealed position. As illustrated in FIG. 24, this is enabled by stopper flange 333 which is an outwardly protruding portion of the plunger shaft 338 positioned above the first bung (as shown in FIG. 23). When the plunger shaft 338 is pulled back towards its proximal end 339, the stopper flange 333 catches the first bung 360 and dislodges the bung from its sealed position. The top compartment 320, the middle compartment 321, and the bottom compartment 322 are now in communication with one another so that the contents of the three compartments can mix.

During this operation, the plunger's 330 travel is limited by a second stopper tab 334 so that a substantial portion of the plunger shaft 338 remains within the middle compartment 321 when the plunger head 332 disengages from the top-compartment sidewall 302 and the three compartments are in communication with one another. When the syringe device 300 is shaken vigorously to mix the contents, the presence of a substantial portion of the plunger shaft 338 facilitates the mixing of the contents by functioning as an agitator. As discussed above in reference to the syringe device 100 of FIG. 4, this agitating function of the plunger shaft 338 may be further enhanced by providing vanes 331 in the portion of the plunger shaft that is positioned within the middle compartment 321.

In an embodiment of the three-compartment syringe that is pre-filled by lyophilization, the disengaging of the plunger head 332 from the top-compartment sidewall 302 may be accomplished by an alternative method. In this alternative method, the user simply unseals the top-end opening 324 of the syringe device 300 by unscrewing the cap 350. In this embodiment, the lyophilization process creates a vacuum condition in the bottom compartment 322 and the vacuum in the bottom compartment 322 pulls on the plunger head 332. But because the top compartment 320 is filled with liquid and sealed air-tight, the plunger head 332 is prevented from being sucked into the bottom compartment 322.

Then, when the cap 350 is unscrewed from the top-end opening 324, the pressure inside the top compartment 320 will equalize with the atmospheric pressure and cause the plunger head 332 to be abruptly sucked into the bottom compartment 322 breaking the seal separating the two compartments. This abrupt breaking of the seal causes the liquid from the top compartment 320 to gush into the bottom compartment 322 enhancing the mixing of the liquid and the dry contents of the bottom compartment 322.

Once the contents of the syringe device 300 is completely mixed and the medicament is ready for dispensing, the syringe device 300 is oriented so that the top compartment is pointing downward. This will cause the medicament to drain into the top compartment 320. The volume of the three components of the medicament preferably is controlled so that the mixed medicament would fit completely inside the top compartment 320 without overflowing. This minimizes any portion of the medicament from being wasted.

Next, while maintaining the top-compartment oriented down, the plunger 330 is pushed down until the plunger head 332 sealingly engages the top-compartment sidewall 302. The syringe device 300 then may be turned into the orientation with the top end of the syringe device 300 pointing upwardly. Then, as shown in FIG. 25, the cap 350 may be removed and a syringe needle 380 may be attached to the top-end opening 324. In this configuration, the syringe device 300 operates similar to a standard syringe. To completely dispense the medicament contained in the top compartment 320, the plunger 330 is fully depressed into the syringe device 300 as illustrated in FIG. 26. It would be apparent to one of ordinary skill in the art that the syringe device 300 may be provided with a dispensing apparatus other than a syringe needle for dispensing the medicament.

As described above with reference to the two-compartment syringe device, one or both of the bungs 340 and 360 in the three-compartment syringe device 300 also may be configured with screw threads so that they may sealingly engage the syringe body 310 by being screwed into their sealed positions. Of course, in this alternate embodiment, the corresponding portions of the syringe body 310 should be provided with screw threads for receiving the bungs 340 and 360.

Most of the seals discussed herein in reference to the various embodiments of the multi-compartment syringe device are described as hermetic seals. However, the quality of the seals may be hermetic or non-hermetic as necessitated by the particular application for the syringe device. The quality of the particular seal in the syringe device can be controlled by selecting appropriate materials for the components that form the seal. The particular physical arrangement or configuration of the components selected will also affect the quality of the seal. For example, in the embodiment of the syringe device where the top-end opening is sealed with a heat sealed membrane, the membrane may be selected from a variety of materials of having varying permeability with respect to air or the particular substance placed inside the top compartment to achieve the desired seal quality at the top-end opening.

It should be emphasized that the above described embodiments of the present invention are merely specific examples. In addition, components and formulations other than medicaments may be administered with the syringe. Various modifications may be made by those skilled in the art which will embody the principles of the invention and fall within the spirit and the scope thereof.

We claim:

1. A syringe device comprising:
   a syringe body having an opening at each of its top and bottom ends;
   a shoulder provided between the top and the bottom ends defining a top-compartment sidewall portion between the top end and the shoulder;
   the shoulder further defining a bottom-compartment sidewall portion between the shoulder and the bottom end;
   the bottom-compartment sidewall portion having a larger cross-section than the top-compartment sidewall portion;
   a plunger having a shaft, a distal end, a proximal end, and a plunger head provided at the distal end;
   the plunger inserted into the syringe body plunger head first through the bottom-end opening;
   the plunger head configured and adapted to form a seal when the plunger head engages the top-compartment sidewall, wherein the plunger is axially translatable between a first position where the plunger head is sealingly engaged with the top-compartment sidewall dividing the syringe body into a top compartment and a bottom compartment, and a second position where the plunger head disengages from the top-compartment sidewall establishing a flow communication between the top and bottom compartments; and a bottom closure member having a central aperture in which the plunger shaft is slidably disposed, wherein the bottom closure member is slidable along the plunger shaft between an unsealed position where the bottom-end opening is not sealed and a sealed position sealing the bottom-end opening of the syringe body.

2. A syringe device according to claim 1, wherein the syringe body's internal shape is tubular.

3. A syringe device according to claim 1, wherein the plunger head forms a hermetic seal with the top-compartment sidewall.

4. A syringe device according to claim 1, wherein the bottom closure member, when in its sealed position, hermetically seals the bottom-end opening of the syringe body.

5. A syringe device according to claim 1, wherein the bottom closure member seals the bottom-end opening of the syringe body by being screwed onto the syringe body.

6. A syringe device according to claim 1, wherein the bottom closure member is a bung having at least one sealing ribs on its outer surface that forms a seal with the bottom-compartment sidewall when the bung is inserted into the bottom-end opening of the syringe body.

7. A syringe device according to claim 1, further comprising a base ridge provided between the shoulder and the bottom end further defining a base-skirt portion, having a larger diameter than the bottom-compartment sidewall portion, between the base ridge and the bottom end of the syringe body, wherein the bottom closure member is a bung having at least one sealing ribs on its outer surface that forms a seal with the base-skirt portion when the bung is inserted into the bottom-end opening of the syringe body.

8. A syringe device according to claim 1, further comprising a top sealing member for sealing the top-end opening of the syringe body that is readily removable to dispense the contents of the syringe device.

9. A syringe device according to claim 8, wherein the top sealing member is a screw cap having screw threads and seals the top-end opening by being screwed onto the top-end opening.

10. A syringe device according to claim 8, wherein the top sealing member is a membrane that is heat-sealed to the top-end opening.

11. A syringe device according to claim 1, wherein at least a portion of the plunger shaft, located within the bottom compartment when the plunger is in its second position, is provided with a plurality of vanes oriented axially along the shaft.

12. A syringe device according to claim 1, wherein the plunger is provided with a thumb rest at its proximal end.

13. A syringe device according to claim 1, wherein the bottom closure member is a bung provided with screw threads on its outer surface and the inside surface of the syringe body near the bottom-end opening is provided with mating screw threads so that the bung screws into the bottom-end opening of the syringe body to seal the bottom-end opening.

14. A syringe device according to claim 1, wherein the bottom closure member is made of an elastomer.

15. A syringe device according to claim 5, wherein the bung has a plurality of outer sealing ribs on its outer surface that sealingly engage the base-skirt portion and a plurality of sealing ribs on the central aperture that sealingly engage the plunger shaft.

16. A syringe device according to claim 1, wherein the plunger head is made of an elastomer.

17. A syringe device according to claim 8, wherein a liquid substance is stored in the top compartment and a dry substance is stored in the bottom compartment.

18. A method of filling a syringe device of claim 1 comprising:
    inserting the plunger into the syringe body plunger head first from the bottom-end opening of the syringe body until the plunger head sealingly engages the top-compartment sidewall portion;
    introducing a first component of a medicament through the top-end opening;
    sealing the top-end opening with a removable top sealing member;
    orienting the syringe body so that the bottom-end opening is directed upwardly;
    introducing a second component of a medicament into the bottom compartment through the bottom-end opening; and
    sealing the bottom-end opening with a bottom closure member.

19. A method of filling a syringe device according to claim 18, wherein the bottom closure member screws onto the bottom-end opening to seal the bottom-end opening.

20. A method of filling a syringe device according to claim 18, wherein the bottom closure member is a bung and the bottom-end opening is sealed by screwing the bung into the bottom-end opening.

21. A method of filling a syringe device according to claim 18, wherein the removable top sealing member is a screw cap.

22. A method of filling a syringe device according to claim 18, wherein sealing the top-end opening includes heat sealing the top-end opening with a membrane, that can be peeled away to unseal the top-end opening.

23. A syringe device comprising:
    a syringe body having an opening at each of its top and bottom ends;
    a shoulder provided between the top and the bottom ends defining a top-compartment sidewall portion between the top end and the shoulder;
    at least one middle ridge located between the shoulder and the bottom end defining a middle-compartment sidewall portion between the shoulder and the middle ridge, and a bottom-compartment sidewall portion between the middle ridge and the bottom end;
    the top-compartment sidewall portion, the middle-compartment sidewall portion and the bottom-compartment sidewall portion having successively larger diameters;
    a plunger having a shaft, a distal end, a proximal end, and a plunger head provided at the distal end;
    the plunger inserted into the syringe body plunger head first through the bottom end opening;
    the plunger head configured and adapted to form a slidable hermetic seal when the plunger head engages the top-compartment sidewall,
    wherein the plunger is axially translatable between a first position where the plunger head is sealingly engaged with the top-compartment sidewall defining a top compartment between the top end and the plunger head, and a second position where the plunger head is disengaged from the top-compartment sidewall;
    at least two bungs, each having a central aperture in which the plunger shaft is slidably disposed, wherein one of the at least two bungs is a terminal bung positioned on the plunger shaft between the plunger head and the proximal end for sealingly engaging the bottom end opening of the syringe body, and the other of the at least two bungs is an intermediate bung positioned on the plunger shaft between the plunger head and the terminal bung;

the intermediate bung slidable along the plunger shaft between a sealed position sealingly engaging the at least one middle ridge, providing a partition between the middle compartment and the bottom compartment, and an unsealed position where the middle compartment and the bottom compartment is in flow communication;

the terminal bung slidable along the plunger shaft between a sealed position sealing the bottom-end opening, and an unsealed position; and the plunger axially translatable between the first position and the second position without dislodging the terminal bung from its sealed position, and a flow communication is established among the compartments when the plunger is in the second position.

24. A syringe device according to claim 23, further comprising a base ridge provided between the middle ridge and the bottom end defining a base-skirt portion between the base ridge and the bottom end wherein the terminal bung forms a seal with the base-skirt portion when the terminal bung is inserted into the bottom-end opening.

25. A syringe device according to claim 23, wherein the syringe body's internal shape is tubular.

26. A syringe device according to claim 23, wherein at least one of the bungs is made of an elastomer.

27. A syringe device according to claim 23, wherein at least one of the bungs has a plurality of outer sealing ribs on its outer surface that sealingly engage the base-skirt portion and a plurality of sealing ribs on central aperture to seal against the plunger shaft.

28. A syringe device according to claim 23, wherein at least one of the bungs is provided with screw threads on its outer surface the inside surface of the syringe body is provided with mating screw threads on its inside surface so that the bung screws into the syringe body to the bung's sealed position.

29. A syringe device according to claim 23, wherein the plunger head is made of an elastomer.

\* \* \* \* \*